US010849988B2

(12) United States Patent
Segura et al.

(10) Patent No.: US 10,849,988 B2
(45) Date of Patent: Dec. 1, 2020

(54) HYDROGEL FOR ENGINEERED IMMUNE RESPONSE TO D-CHIRALITY PEPTIDES

(71) Applicant: THE REGENTS OF THE UNIVERSITY OF CALIFORNIA, Oakland, CA (US)

(72) Inventors: Tatiana Segura, Los Angeles, CA (US); Donald Griffin, Los Angeles, CA (US); Philip Scumpia, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 2 days.

(21) Appl. No.: 16/092,202

(22) PCT Filed: Apr. 10, 2017

(86) PCT No.: PCT/US2017/026798
§ 371 (c)(1),
(2) Date: Oct. 8, 2018

(87) PCT Pub. No.: WO2017/177225
PCT Pub. Date: Oct. 12, 2017

(65) Prior Publication Data
US 2019/0142965 A1 May 16, 2019

Related U.S. Application Data

(60) Provisional application No. 62/320,309, filed on Apr. 8, 2016.

(51) Int. Cl.
| | | |
|---|---|---|
| A61K 38/00 | (2006.01) |
| A61K 39/00 | (2006.01) |
| A61K 39/12 | (2006.01) |
| A61K 47/69 | (2017.01) |
| A61K 39/39 | (2006.01) |
| A61L 27/38 | (2006.01) |
| A61L 27/18 | (2006.01) |
| A61L 27/54 | (2006.01) |
| A61L 27/58 | (2006.01) |
| A61L 27/50 | (2006.01) |
| A61L 26/00 | (2006.01) |
| A61L 27/20 | (2006.01) |
| A61L 27/52 | (2006.01) |
| A61L 27/56 | (2006.01) |
| A61K 47/60 | (2017.01) |
| A61P 17/02 | (2006.01) |
| A61K 38/06 | (2006.01) |
| A61K 38/48 | (2006.01) |
| A61K 39/02 | (2006.01) |

(52) U.S. Cl.
CPC .......... *A61K 47/6903* (2017.08); *A61K 38/06* (2013.01); *A61K 38/4886* (2013.01); *A61K 39/0011* (2013.01); *A61K 39/02* (2013.01);
*A61K 39/12* (2013.01); *A61K 39/39* (2013.01); *A61K 47/60* (2017.08); *A61L 26/008* (2013.01); *A61L 26/009* (2013.01); *A61L 26/0019* (2013.01); *A61L 26/0023* (2013.01); *A61L 26/0057* (2013.01); *A61L 26/0066* (2013.01); *A61L 26/0085* (2013.01); *A61L 27/18* (2013.01); *A61L 27/20* (2013.01); *A61L 27/38* (2013.01); *A61L 27/50* (2013.01); *A61L 27/52* (2013.01); *A61L 27/54* (2013.01); *A61L 27/56* (2013.01); *A61L 27/58* (2013.01); *A61P 17/02* (2018.01); *A61K 2039/55516* (2013.01); *A61K 2039/6031* (2013.01); *A61K 2039/6093* (2013.01); *A61K 2039/64* (2013.01); *A61L 2300/214* (2013.01); *A61L 2300/256* (2013.01); *A61L 2400/06* (2013.01)

(58) Field of Classification Search
CPC ........ A61K 38/00; A61K 39/00; A61K 39/02; A61K 39/12
USPC ..... 424/9.1, 9.2, 184.1, 204.1, 234.1, 278.1, 424/400, 422, 428
See application file for complete search history.

(56) References Cited

FOREIGN PATENT DOCUMENTS

| WO | 2015116242 | 8/2015 |
| WO | 2016011387 | 1/2016 |

OTHER PUBLICATIONS

PCT International Search Report & Written Opinion dated Jul. 7, 2017, International Application No. PCT/US2017/026798.
Appavu et al., "Enhancing the Magnitude of Antibody Responses Through Biomaterial Stereochemistry", ACS Biomaterials Science & Engineering, Jun. 12, 2015, vol. 1, pp. 601-609.
Benkirane et al., "Antigenicity and Immunogenicity of Modified Synthetic Peptides Containing D-Amino Acid Residues", Journal of Biological Chemistry, Dec. 15, 1993, vol. 268, pp. 26279-26285.

(Continued)

Primary Examiner — Rodney P Swartz
(74) Attorney, Agent, or Firm — Gates & Cooper LLP

(57) ABSTRACT

An immune-modulating biomaterial comprising a hydrogel scaffold coupled to D-amino acid containing peptides having unexpected properties in vivo is described. For example, certain inflammatory reactions in vivo are significantly increased around the D-peptide containing particles of hydrogel scaffold as compared to particles that contain both L and D peptides or L peptides alone. In addition, these D-peptide compositions are further observed to enhance wound healing and improve the tensile strength of healed tissues. For these and other reasons, the D-amino acid hydrogel materials disclosed herein are useful in a number of methodologies that seek to modulate the immune response and/or wound healing.

13 Claims, 8 Drawing Sheets
Specification includes a Sequence Listing.

(56) References Cited

OTHER PUBLICATIONS

Griffin et al., "Accelerated Wound Healing by Injectable Microporous Gel Scaffolds Assembled from Annealed Building Blocks", Nature Materials, Jul. 1, 2015, vol. 14, pp. 737-744.

Krishnamoorthy et al., "Effect of D-Amino Acids on Collagen Fibrillar Assembly and Stability: Experimental and Modelling Studies", Biochemical Engineering Journal, Jun. 15, 2013, vol. 75, pp. 92-100.

Shi et al, "D-Amino Acids Modulate the Cellular Response of Enzymatic-Instructed Supramolecular Nanofibers of Small Peptides", Biomacromolecules, Sep. 17, 2014, vol. 15, pp. 3559-3568.

International Preliminary Report on Patentability dated Oct. 18, 2018 for PCT Application No. PCT/US2017/026798.

Anti-L peptide IgG3

Anti-D peptide IgG3

Anti-L peptide IgG2a

Anti-D peptide IgG2a

Anti-L peptide IgG1

Anti-D peptide IgG1

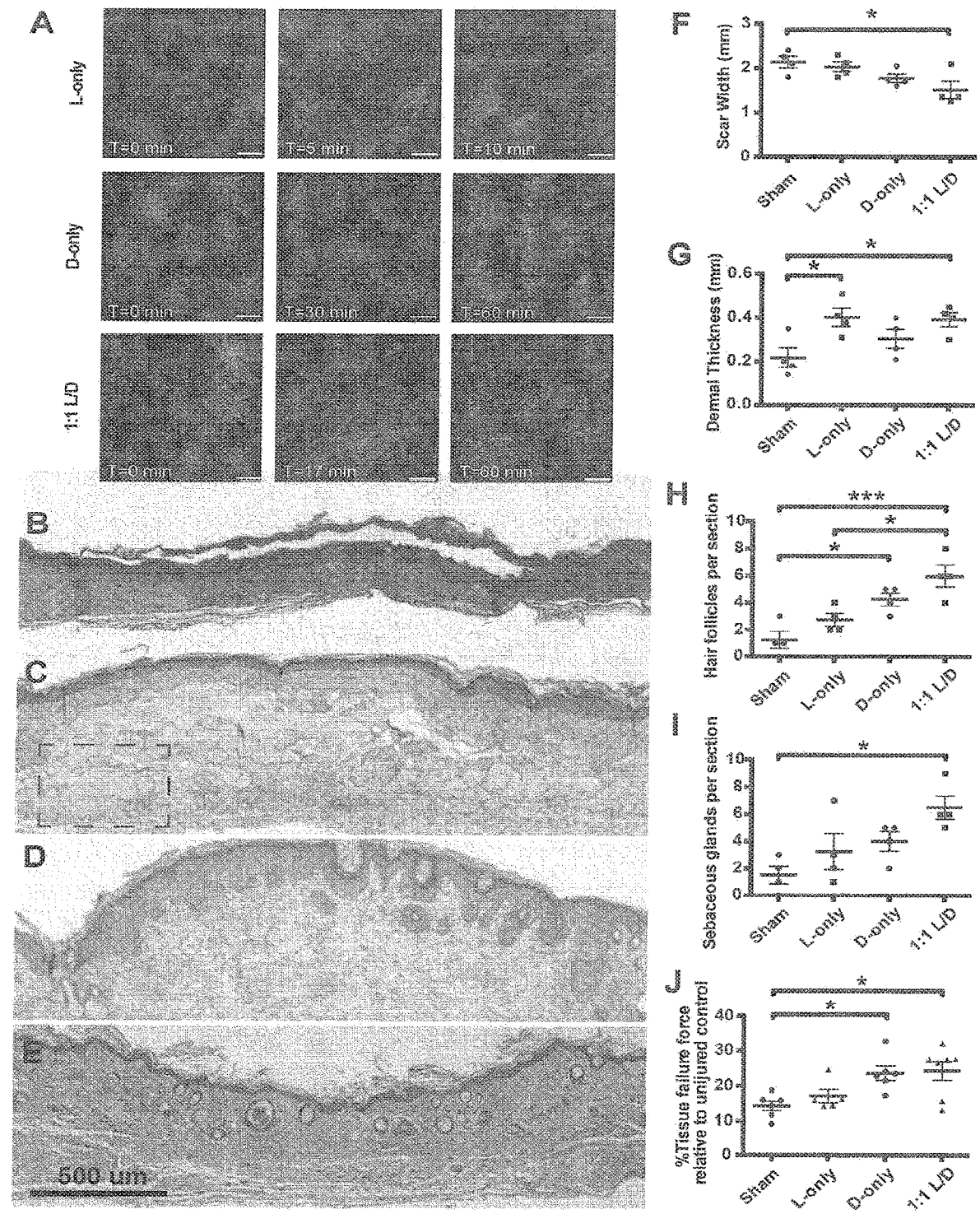
Fig. 5 A-J

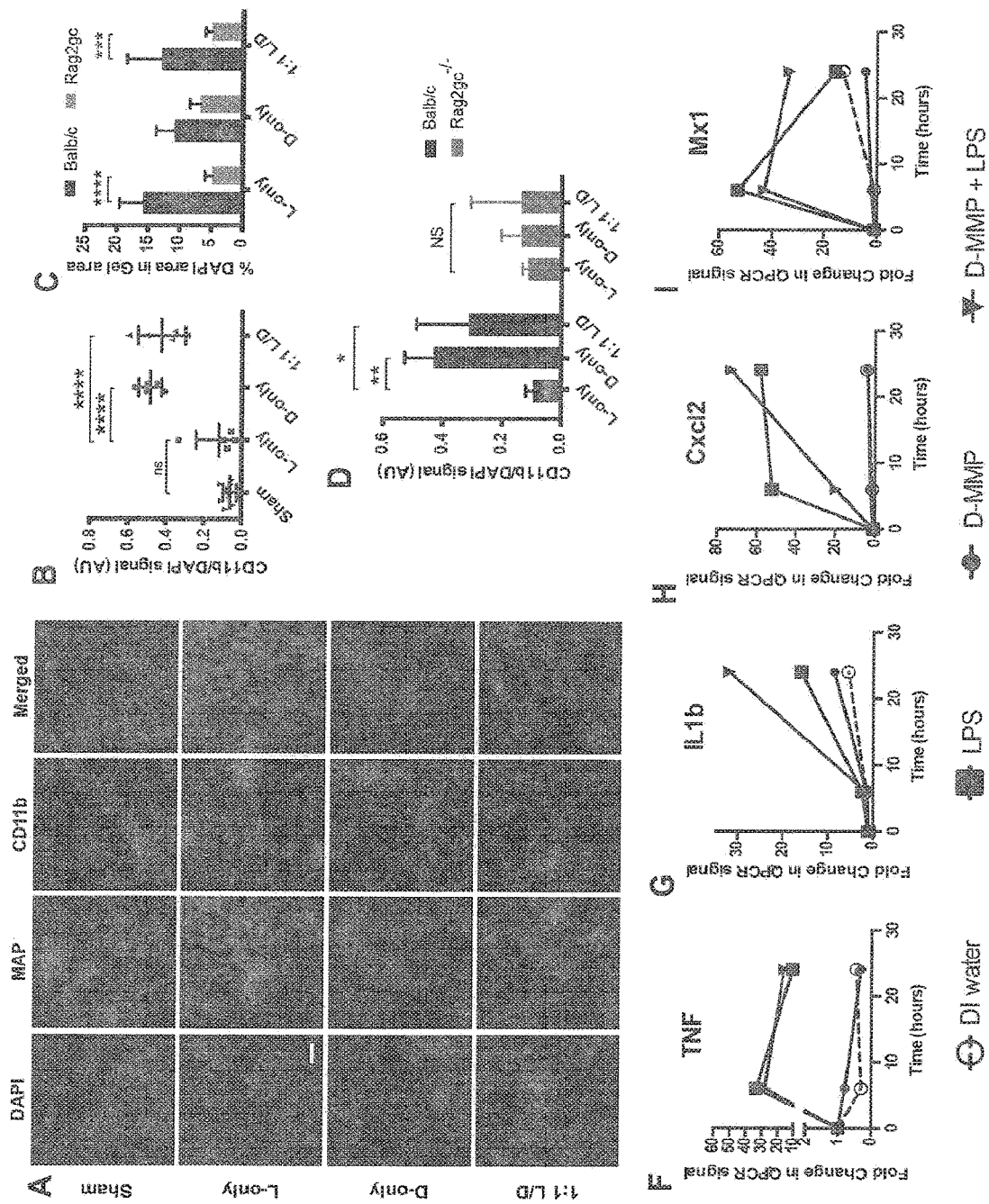
Fig. 6 A-I

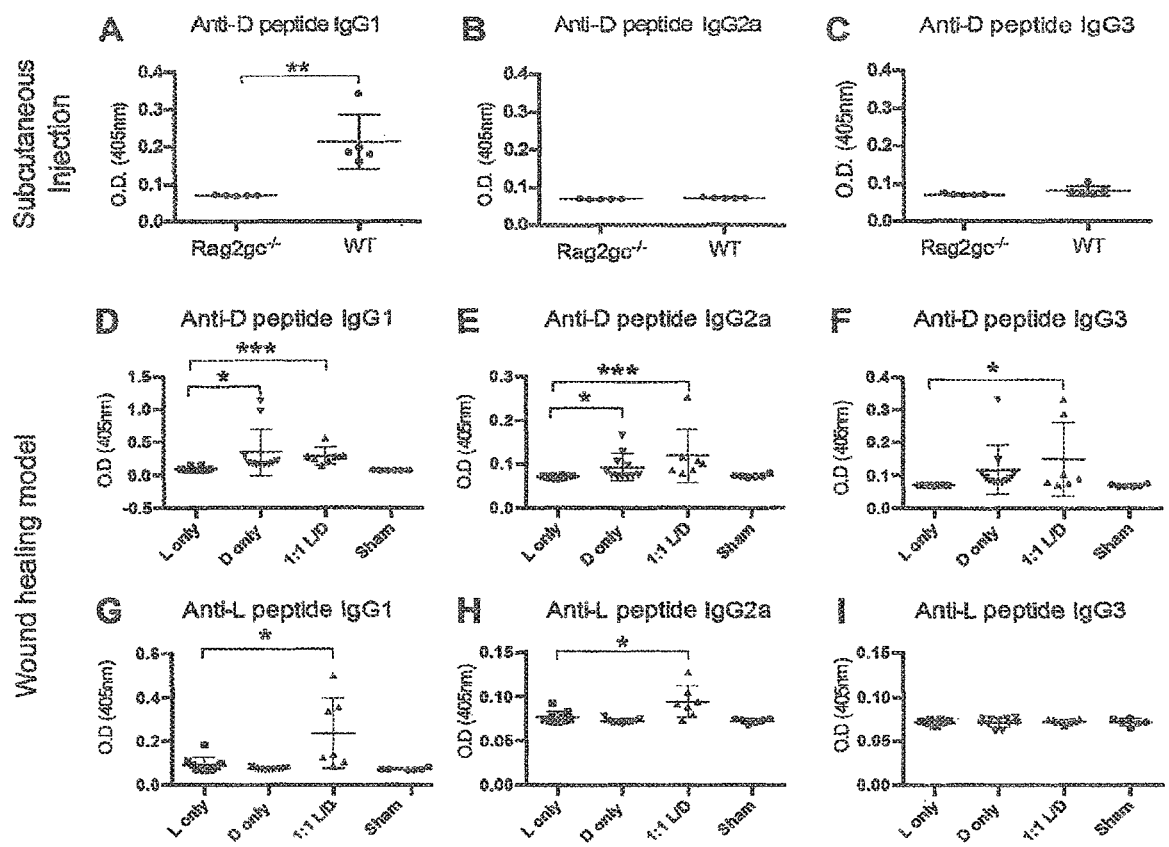
Fig. 7 A-I

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Gly Gly Glu Arg Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Gln Glu Gln Val Ser Pro Leu
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Gln Glu Gln Val Ser Pro Leu Arg Gly Asp Ser Pro Gly
1               5                   10

<210> SEQ ID NO 4

<400> SEQUENCE: 4

000

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Ile Lys Val Ala Val
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Gln
<220> FEATURE:
<221> NAME/KEY: MOD_RES
<222> LOCATION: (9)..(9)
<223> OTHER INFORMATION: D-Ile
<220> FEATURE:
<221> NAME/KEY: MOD_RES
<222> LOCATION: (10)..(10)
<223> OTHER INFORMATION: D-Trp

<400> SEQUENCE: 6

Gly Cys Arg Asp Gly Pro Gln Gly Ile Trp Gly Gln Asp Arg Cys Gly
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Asp Ser Pro Gly Glu Arg Cys Gly
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Cys Arg Asp Gly Pro Gln Gly Ile Trp Gly Gln Asp Arg Cys Gly
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Lys Gly Gly Glu Arg Cys Gly
1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Asn Gln Glu Gln Val Ser Pro Leu Gly Gly Glu Arg Cys Gly
1               5                   10
```

US 10,849,988 B2

HYDROGEL FOR ENGINEERED IMMUNE RESPONSE TO D-CHIRALITY PEPTIDES

REFERENCE TO RELATED APPLICATIONS

This application claims priority under Section 119(e) from U.S. Provisional Application Ser. No. 62/320,309, filed Apr. 8, 2016, entitled "HYDROGEL FOR ENGINEERED IMMUNE RESPONSE TO D-CHIRALITY PEPTIDES" by Tatiana Segura et al., the contents of which are incorporated herein by reference.

STATEMENT REGARDING FEDERALLY SPONSORED RESEARCH AND DEVELOPMENT

This invention was made with Government support under R01NS079691 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on May 24, 2017, is named 30435_313-WO-U1_SL.txt and is 2,683 bytes in size.

TECHNICAL FIELD

The invention relates to immunology and in particular, immune modulation and immunotherapy.

BACKGROUND OF THE INVENTION

Immune modulation is an area of increasing interest for biomedical applications. This includes, but is not limited to, areas of wound healing, cancer treatment, and vaccine delivery. The immune system is involved in orchestrating the healing cascade following injury and in the adapted response to both malignant growths (e.g. cancer) and foreign pathogens. Immune modulation or immunotherapy is an approach to treating diseases and/or improving healing by inducing, enhancing, or suppressing an immune response. In this context, biomaterials that can modulate the immune response and improve healing are highly desirable.

The creation of biomaterials that can modulate an immune response in a beneficial manner (e.g. improve healing, eliminate malignant cancers, etc.) is of particular interest to those in a variety of medical fields due to, for example, the extended exposure a solid material has as compared to liquid solutions (which are quickly cleared and eliminated from the body through the urinary tract). In addition, solid or semi-solid biomaterial-based materials such as hydrogels are particularly useful as they can be localized to specific tissues or regions of the body in which they are most efficacious.

A relatively new class of injectable biomaterials-microporous annealed particle (MAP) gels has shown promise in accelerated wound healing (see, e.g. Griffin et al., Nat Mater. 2015 July; 14(7):737-44). Such materials can circumvent the need for material degradation before tissue ingrowth by providing a stably linked interconnected network of micropores for cell migration and bulk integration with surrounding tissue. Such materials can be designed to include lattices of microgel building blocks are then annealed to one another via surface functionalities to form an interconnected microporous scaffold. These MAP scaffolds can be injected and moulded to any shape providing a mechanically stable scaffold of interconnected micropores for cell migration and bulk integration with surrounding tissue.

As is known in this art, the biological activity of bioactive agents can be effected by a variety of factors such as the specific combination of bioactive ingredients in the formulation, the medium in which they are delivered, and the route of delivery. In this context, the ways that microporous gel scaffolds may (or may not) effect various activities of bioactive agents in vivo is unpredictable and difficult to discern. For this reason, there is a need in the art for new combinations of materials and agents that have been proven to be efficacious in modulating crucial physiological phenomena such as the immune response and would healing.

SUMMARY OF THE INVENTION

As discussed in detail below, we have developed an immune-modulating biomaterial comprising a hydrogel scaffold coupled to D-chirality peptides. In vivo studies of this material show that it exhibits a number of unexpected and desirable properties. For example, we have discovered that inflammatory reactions in vivo are significantly increased around the D-amino acid peptide containing particles of hydrogel scaffold as compared to equivalent particles that contain L-amino acid peptides alone. In addition, these D-peptide containing particle materials are further observed to enhance wound healing and improve the tensile strength of healed tissues. For these and other reasons, the D-amino acid hydrogel materials disclosed herein are useful in a number of methodologies that seek to modulate the immune response and/or wound healing. Illustrative embodiments of the invention are discussed in the following sections.

The invention disclosed herein has a number of embodiments. Embodiments of the invention include compositions comprising a polymeric hydrogel scaffold coupled to an adjuvant peptide comprising at least one D amino acid and an immunogenic peptide comprising a viral, bacterial or cancer immunogen recognized by human immune cells. Typically in these compositions, the adjuvant peptide and the immunogenic peptide are disposed in the polymeric hydrogel scaffold such that an in vivo immune reaction observed in human immune cells exposed to the immunogenic peptide is greater than an immune reaction observed in response to an equivalent polymeric hydrogel scaffold composition having peptides formed only from L amino acids (i.e. a comparative control composition comprising the same polymeric hydrogel scaffold coupled to an adjuvant peptide comprising only L-amino acids and an immunogenic peptide comprising only L-amino acids which form a viral, bacterial or cancer immunogen recognized by human immune cells).

In typical embodiments of the invention, the polymeric hydrogel scaffold surrounds and encapsulates the immunogenic peptide. Optionally, the adjuvant peptide comprises a crosslinker forming part of a backbone structure of the hydrogel scaffold. In certain embodiments, the polymeric hydrogel scaffold forms pores in the composition, and the pores are between 1 μm and 50 μm such that immune cells can infiltrate the composition. In this context, certain embodiments of the further human or murine immune cells (e.g. which have migrated into the cell from an external in vivo or in vitro environment).

The D-amino acid containing peptide compositions of the invention are observed to exhibit a number of surprising properties in vivo. For example, in typical embodiments of the invention, the immunogenic peptide is disposed in the polymeric hydrogel scaffold such that an amount of CD11b+ immune cells that infiltrate into the composition in vivo is at least 50% greater than an amount of CD11b+ immune cells observed in response to an equivalent polymeric hydrogel scaffold composition having peptides formed only from L amino acids. In certain embodiments of the invention, the immunogenic peptide the immunogenic peptide is disposed in the polymeric hydrogel scaffold such that a titer of antibodies generated against the anti-antigenic peptide (e.g. IgG1 antibodies) is at least 50% greater than a titer of antibodies generated in response to an equivalent polymeric hydrogel scaffold composition having peptides formed only from L amino acids.

Embodiments of the invention include methods of using the compositions disclosed herein to modulate one or more physiological processes in vitro or in vivo. On such embodiment is a method of modulating an immune response comprising contacting human immune cells with a composition disclosed herein (e.g. compositions comprising a polymeric hydrogel scaffold coupled to an adjuvant peptide comprising at least one D amino acid and an immunogenic peptide comprising a viral, bacterial or cancer immunogen recognized by human immune cells) so that the cells recognize the immunogenic peptide and initiate an immune response to the immunogenic peptide.

Another methodological embodiment of the invention is a method of increasing the tensile strength of new tissue forming in a wound comprising contacting the wound with a composition disclosed herein comprising a polymeric hydrogel scaffold and peptide comprising at least one D amino acid. Typically in these methods, the tensile strength of tissue in the healed wound as measured by a tensiometer is at least 50% greater than a wound contacted with an equivalent composition comprising a polymeric hydrogel scaffold coupled to a peptide comprising only L amino acids.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 2A shows the results from different fluorescent stains (DAPI, MAP-Alexa488, CD11b, and all three stains merged). FIG. 2B is a graph comparing CD11b response to MAP gel at day 21. As shown in this data, the inflammatory reaction is significantly increased around the D-peptide containing particles. However, in particles that contain both L and D peptides (Hom) no activation is observed. This tissue was retrieved from a full thickness skin wound of a mouse model. The 1:1 50% D Het is a mixture of hydrogel particles where half of the particles are crosslinked with 100% L-chirality or D-chirality crosslinker. The 1:1 50% D Hom is a mixture of hydrogel particles where every particle is identically composed of 50% of the crosslinker being D-chirality and 50% being L-chirality.

FIG. 3F, the bottom right sub-figure shows an IgG-1 antibody (indicative of T-cell dependency) recognition of the D-peptide in only mice exposed to the D-peptide gel. FIG. 3E, the bottom left sub-figure is, at least, equally exciting as it shows the production of an L-specific antibody in only the mouse that was exposed to D+L and not in the L only mouse. This data provides evidence that D MAP gels act as an adjuvant, a crucial element for antibody production in vaccines (i.e. by increasing the efficacy of one-time vaccine delivery).

FIGS. 5A-5J show data from studies on D and L peptide MMP sensitivity to enzyme degradation in vitro. FIG. 5 A) Comparison of MMP sensitivity to enzyme degradation in vitro, showing that the L-only gel degrades within 10-20 minutes (seen by disappearance of microgels), while the D-only microgels (shown in red) remain unaffected even after 1 hour exposure to equal amount of enzyme. B) H&E of untreated wound with condensed scar tissue. C) H&E of L-only MAP treated wound showing large volume of remaining hydrogel (light pink blobs). D) H&E of D-only MAP treated wound showing complete disappearance of gel and significant number of new tissue structures (relative to L-only MAP). E) 1:1 ratio of L and D microgels treated wound showing complete absence of gel and very normal tissue architecture. F-I) Pathology evaluations of tissue quality. J) Strength of wound area tissue under tensile testing relative to unwounded skin (internal control).

FIGS. 6A-6I show data from comparative studies on D and L peptides. FIG. 6A) Visual of CD11b positive cells (immune cells) within and around gel (shown in red) within a healed dermal wound bed at Day 21 comparing Sham, L-only, D-only, and 1:1 L/D samples, showing the D-peptide containing MAP recruits high numbers of CD11b positive cells. Note: in 1:1 L/D samples the L gels are unlabeled. FIG. 6B) Quantification of CD11b positive cells (immune cells) within and around gel within a healed dermal wound bed at Day 21 (ex. FIG. 6A). FIG. 6C) Comparing cell recruitment into subcutaneously-injected gels as a function of adaptive immune competence (Balb/c) versus adaptive immune incompetence (Rag2gc−/−). FIG. 6D) Fraction of immune cell to total cell recruitment within a subcutaneously injected gels as a function of adaptive immune competence (Balb/c) versus adaptive immune incompetence (Rag2gc−/−). FIGS. 6E-I) mRNA production of key markers of inflammation within an in vitro macrophage assay upon exposure to DI water, Lipid Polysaccharide (LPS) 500 ug/mL, D-MMP crosslinker 500 ug/mL, and LPS+D-MMP. These figures show that D-MMP has no direct effect on the macrophages relative to the positive control (LPS), but does have some additive affects when combined with the positive control (LPS).

FIGS. 7A-7I show data from comparative studies on D and L peptides, in particular ELISA analysis of specific antibody production against the D peptide (A-F) or L-peptide (G-I). A-C) Antibody production within mice exposed to subcutaneous injections of MAP containing D-peptide (150 uL total) after 21 days, comparing mice with adaptive immune competency WT) versus incompetency (Rag2gc−/−). D-I) Antibody production within mice exposed to MAP containing either L-only, D-only, 1:1 L/D within a dermal wound healing model (150 uL total) after 21 days (sham/untreated wounds included as negative control).

DETAILED DESCRIPTION OF THE INVENTION

Figure 1:
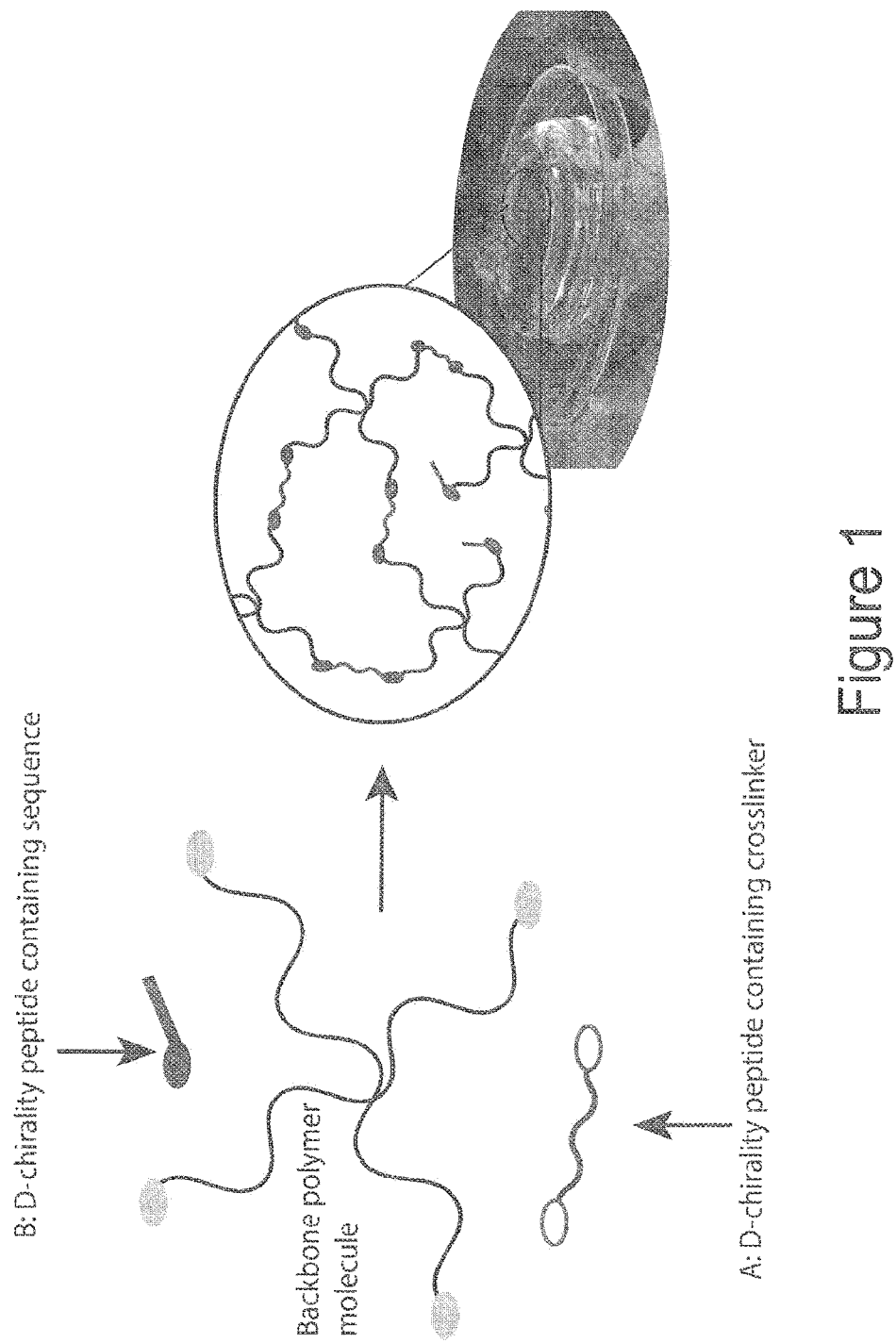
FIG. 1 illustrates D-chirality amino acid incorporation into a hydrogel, in accordance with one or more embodiments of the invention. The D-chirality amino acids can be incorporated as either a crosslinker that becomes part of the hydrogel backbone structure (indicated with arrow A) and/or as a covalently or non-covalently backbone-attached peptide sequence (indicated with arrow B).

In the description of the illustrative embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patents, and patent applications cited herein are hereby incorporated by reference in their entirety for all purposes.

The evolution of materials for use in medical fields such as immunological and regenerative medicine has been driven by a variety of needs which depend upon the in vivo activity that the material is designed to modulate. Optimization of these materials has typically been focused on tuning their bulk properties to regulate cell behaviour through material stiffness and chemical moieties, such as oligopeptides and growth factors. These approaches are limited by physical constraints, as host cells remodel this precisely tuned matrix to infiltrate the material, and by the unpredictable ways in which this material can influence the activities of bioactive agent disposed in such hydrogels. The invention disclosed herein builds upon these studies and is based upon the surprising discovery that inflammatory reactions in vivo are significantly increased around the D-peptide containing particles of hydrogel scaffold as compared to particles that contain both L and D peptides or L peptides alone. This finding is unexpected in view of art in this technology that teaches that in conventional compositions known in the art, the selection of D enantiomers can be used to decrease immunogenicity of peptides as compared to L-enantiomers having the same sequences (see, e.g., U.S. Patent Publication 2011/0189290, the contents of which are incorporated by reference).

Methods and materials that can be adapted for use with embodiments of the invention disclosed herein include those described in Griffin et al., "Accelerated Wound Healing by Injectable Microporous Gel Scaffolds Assembled from Annealed Building Blocks." Nature Materials 2015 July; 14(7):737-44 and U.S. Patent Publication 2015/0104427, the contents of which are incorporated by reference.

The invention disclosed herein has a number of embodiments. Embodiments of the invention include compositions comprising a polymeric hydrogel scaffold coupled to an adjuvant peptide comprising at least one D amino acid and an immunogenic peptide comprising a viral, bacterial or cancer immunogen recognized by human immune cells. Typically in these compositions, the adjuvant peptide and the immunogenic peptide are disposed in the polymeric hydrogel scaffold such that an in vivo immune reaction observed in human immune cells exposed to the immunogenic peptide is greater than an immune reaction observed in response to an equivalent polymeric hydrogel scaffold composition having peptides formed only from L amino acids (i.e. a comparative control composition comprising a polymeric hydrogel scaffold coupled to an adjuvant peptide comprising only L-amino acids and an immunogenic peptide comprising only L-amino acids which form a viral, bacterial or cancer immunogen recognized by human immune cells).

In typical embodiments of the invention, the polymeric hydrogel scaffold surrounds and encapsulates the immunogenic peptide. Optionally, the adjuvant peptide comprises a crosslinker forming part of a backbone structure of the hydrogel scaffold. In certain embodiments, the polymeric hydrogel scaffold forms pores in the composition, and the pores are between 1 µm and 50 µm (e.g. between 10 µm and 30 µm) such that immune cells can infiltrate the composition. In this context, certain embodiments of the further human or murine immune cells (e.g. which have migrated into the cell from an external in vivo or in vitro environment). Optionally, the adjuvant peptide and the immunogenic peptide comprise an identical segment of at least 6 amino acids, or alternatively do not comprise an identical segment of at least 6 amino acids. The compositions of the invention can include a variety of elements such as those that modulate the architecture of the scaffold. Optionally, the hydrogel scaffold comprises at least one of polyethylene glycol polymers, hyaluronic acid polymers, an RGD peptide, a Q peptide, a K peptide, or a Matrix Metallo-protease (MMP) peptide.

As shown in the data presented in the figures, the compositions of the invention are observed to exhibit a number of unexpected properties. For example, in typical embodiments of the invention, the immunogenic peptide is disposed in the polymeric hydrogel scaffold such that an amount of CD11b$^+$ immune cells that infiltrate into the composition in vivo is at least 50% greater than an amount of CD11b$^+$ immune cells observed in response to an equivalent polymeric hydrogel scaffold composition having peptides formed only from L amino acids. CD11b is expressed on the surface of many leukocytes including monocytes, neutrophils, natural killer cells, granulocytes and macrophages. Functionally, CD11b regulates leukocyte adhesion and migration to mediate the inflammatory response. CD11b antibody studies have shown the protein to be directly involved in cellular adhesion, although migration can only take place in the presence of the CD18 subunit. In certain embodiments of the invention, the immunogenic peptide the immunogenic peptide is disposed in the polymeric hydrogel scaffold such that a titer of antibodies generated against the anti-antigenic peptide (e.g. IgG1 antibodies) is at least 50% greater than a titer of antibodies generated in response to an equivalent polymeric hydrogel scaffold composition having peptides formed only from L amino acids.

Embodiments of the invention include methods of using the compositions disclosed herein to modulate one or more physiological processes in vitro or in vivo. On such embodiment is a method of modulating an immune response comprising contacting human immune cells with a composition disclosed herein (e.g. compositions comprising a polymeric hydrogel scaffold coupled to an adjuvant peptide comprising at least one D amino acid and an immunogenic peptide comprising a viral, bacterial or cancer immunogen recognized by human immune cells) so that the cells recognize the immunogenic peptide and initiate an immune response to the immunogenic peptide. In certain embodiments, this immune response comprises an infiltration of $CD11b^+$ cells to the site of the composition. Typically in these methods, the amount of $CD11b^+$ immune cells that infiltrate into the composition in vivo is at least 50% greater than an amount of $CD11b^+$ immune cells observed in response to an equivalent polymeric hydrogel scaffold composition having peptides formed only from L amino acids. In certain embodiments, the immune response comprises generating a titer of IgG1 antibodies that is at least 50% greater than a titer of IgG1 antibodies generated in response to an equivalent polymeric hydrogel scaffold composition having peptides formed only from L amino acids. Typically in these methods, the composition is disposed in a wound.

Figure 4:
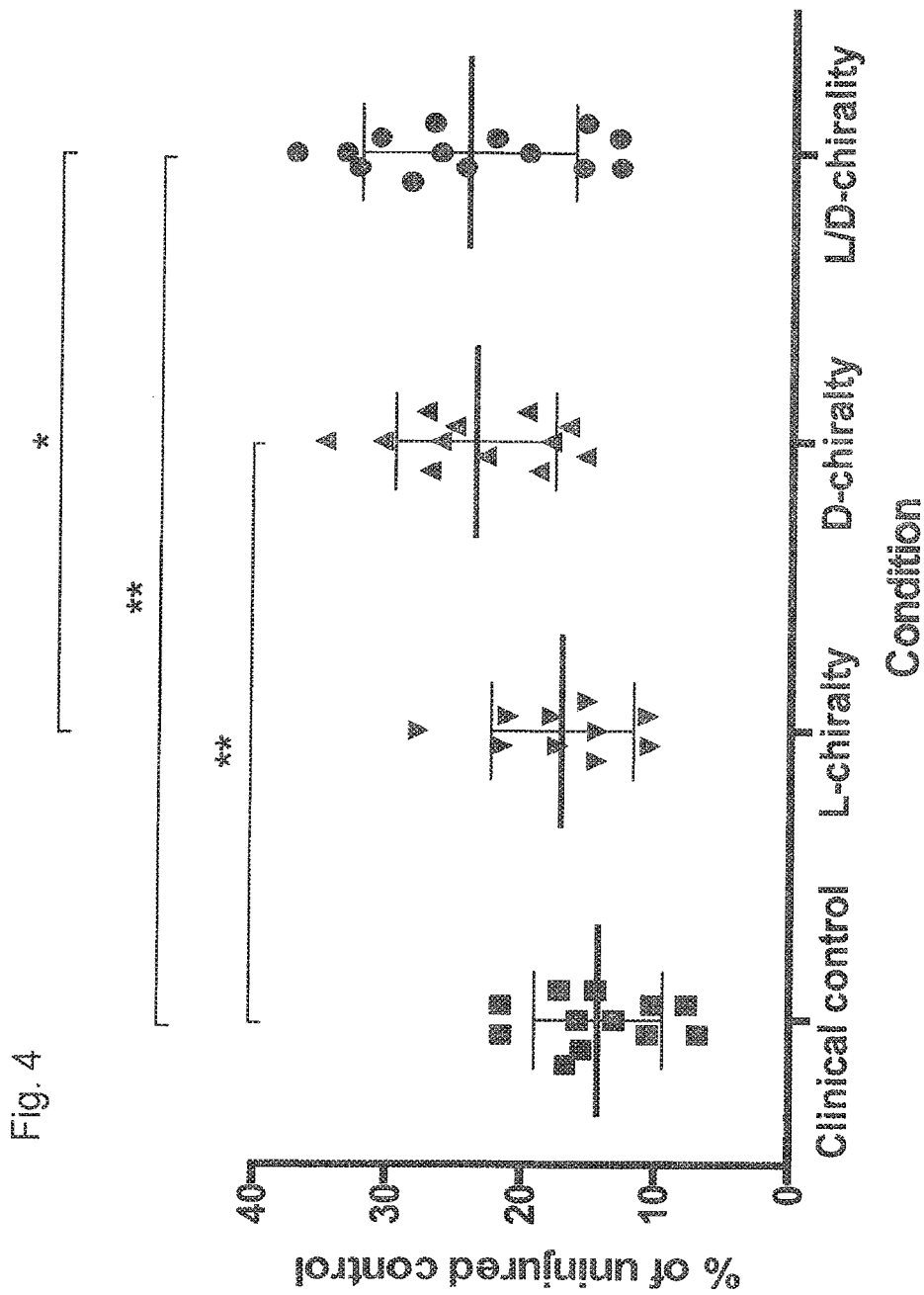
FIG. 4 shows data from D and L peptide tensiometry experiments where different microporous annealed particle (MAP) D and/or L peptide compositions were injected in wounds mice and the tensile strengths of the respective healed wounds then measured. This data shows an increased tensile maximum failure strength in wounds healed using the D MAP gels as compared to wounds healed using L-peptide compositions. This increased maximum failure strength is indicative of better overall functional tissue regeneration as one of the primary modes of scar failure is tearing at the site of an old wound. In these experiments, the mice were wounded and the wound was filled with MAP gel or an emoliant (clinical equivalent). Following a 21-day healing window the skin was removed and placed under tensile strain until failure (and this failure force was recorded as shown in the presented data).

Another embodiment of the invention is a method of increasing the tensile strength of new tissue forming in a wound comprising contacting the wound with a composition disclosed herein comprising a polymeric hydrogel scaffold and peptide comprising at least one D amino acid (see, e.g. the data from illustrative working embodiments that is presented in FIG. 4). Optionally, the composition comprises a polymeric hydrogel scaffold coupled to an adjuvant peptide comprising at least one D amino acid and an immunogenic peptide comprising a viral, bacterial or cancer immunogen recognized by human immune cells. Typically in these compositions, the adjuvant peptide and the immunogenic peptide are disposed in the polymeric hydrogel scaffold such that an in vivo immune reaction observed in human immune cells exposed to the immunogenic peptide is greater than an immune reaction observed in response to an equivalent polymeric hydrogel scaffold composition having peptides formed only from L amino acids. Optionally the adjuvant peptide comprises a crosslinker forming part of a backbone structure of the hydrogel scaffold; and/or the polymeric hydrogel scaffold surrounds and encapsulates the immunogenic peptide; and the polymeric hydrogel scaffold forms pores in the composition, and the pores are between 1 μm and 50 μm (typically between 10 μm and 30 μm) such that mammalian cells can infiltrate the composition.

Typically in these methods, the tensile strength of tissue in the healed wound as measured by a tensiometer is at least 50% greater than a wound contacted with an equivalent composition comprising a polymeric hydrogel scaffold coupled to a peptide comprising only L amino acids (see, e.g. data from working embodiments of the invention that is presented in FIG. 4). In this context, a variety of methods for measuring the tensile strength of tissue can be used to observe this aspect of the invention. See, e.g. Chao et al., J Biomech Eng. 2013 Oct. 1; 135(10)101009-8, Chang et al., J Anesth. 2010 April; 24(2):240-6; Fritz et al., Ann Plast Surg, 2012 October; 69(4):462-7, and U.S. Patent Publications 20080076112 and 20130017175, the contents of which are incorporated by reference.

Certain embodiments of the invention can include peptides useful to control the properties of the adjuvant compositions. As used herein, "peptide" may refer to fragments of polypeptides and/or short polypeptides and/or polypeptides. Compositions of the invention include a hydrogel in combination with a bioactive signal. As used herein, "bioactive signal(s)" refers to compounds having a biological activity designed to modulate the function of a hydrogel composition in vivo and can refer to an adjuvant peptide having an amino acid sequence comprising one or more D amino acids (and which functions as an adjuvant in immune reactions), and/or an immunogenic peptide. As used herein, adjuvant refers to a compound that is selectively used in a vaccine composition in order to modify the immune response by boosting it such as to give a higher amount of antibodies. One or more of the bioactive signals useful in the compositions of the invention are typically peptides.

As used herein, "K peptide(s)" preferably refers to a peptide sequence having K (i.e., amino acid lysine). For example, K peptide may refer to the peptide sequence FKG and/or peptide sequences having FKG, i.e., Ac-FKGGERC-$NH_2$ (SEQ ID NO: 1). The K peptide may be identified through a rational peptide library (see, e.g., Hu B H, Messersmith P B. Rational design of transglutaminase substrate peptides for rapid enzymatic formation of hydrogels. *J Am Chem Soc* 2003 Nov. 26; 125(47): 14298-14299). As used herein, "Q peptide(s)" (i.e., amino acid glutamine) preferably refers to the peptide sequence NQEQVSPL (SEQ ID NO: 2) and/or sequences containing NQEQVSPL (SEQ ID NO: 2). Typically, the Q peptide is the sequence recognized by FXIIIa in plasminogen inhibitor α2PI. As used herein, "Q peptide-RGD" may refer to H-NQEQVSPL-RGDSPG-$NH_2$ (SEQ ID NO: 3) and/or any other sequence having Q peptide as defined herein and having the peptide sequence RGD (the amino acid sequence arginine-glycine-aspartic acid). In other embodiments, Q peptide may refer to any peptide sequence having Q.

As used herein, "bioactive signal(s)" may also refer to the peptide sequence RGD and/or may refer to the peptide sequence RGD linked and/or bonded with and/or attached to the Q or other peptides as defined therein. As such, "bioactive signal" may refer to the Q peptide-RGD sequence. "Bioactive signal" may refer to any other bioactive signal linked and/or bonded with and/or attached to the Q peptide as defined herein. For example, it may refer to the sequence Q peptide-D amino acid peptide adjuvant fragment. In other embodiments, bioactive signal(s) may refer to any other bioactive signal to be immobilized/incorporated in the hydrogel using the methods of the present invention (with or without Q peptide). For example, the bioactive signal may refer to a peptide, such as, but not limited to, a peptide with a protease cleavage site. The bioactive signal may refer to fibronectin or a fragment thereof; and/or the bioactive signal may refer to a growth factor such as VEGF, or the like. Any bioactive signal capable of being immobilized in a hydrogel may be used with the methods disclosed herein. It is to be understood that the bioactive signal used in a single hydrogel may be same or different.

As used herein, "hydrogel" may be interchangeable with "hydrogel scaffold" and/or "scaffold." As used herein, "Factor XIII" and "FXIIIa" are interchangeable. As used herein, "fragment" with reference to a polypeptide/peptide is used to describe a portion of a larger molecule. Thus, a polypeptide fragment may lack an N-terminal portion of the larger molecule, a C-terminal portion, or both. Fragments may include any percentage of the full-length polypeptide/peptide. As used herein, "hydrogel" may refer to any polymeric network and/or any tissue engineering support system. As used herein, the term "support" includes: natural polymeric carbohydrates and their synthetically modified, crosslinked, or substituted derivatives, such as agar, agarose, cross-linked alginic acid, chitin, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins, and keratins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass; and mixtures or copolymers of the above classes, such as graft copolymers obtained by initializing polymerization of synthetic polymers on a preexisting natural polymer. A variety of biocompatible and biodegradable polymers are available for use in therapeutic applications; examples include: polycaprolactione, polyglycolide, polylactide, poly(lactic-co-glycolic acid) (PLGA), and poly-3-hydroxybutyrate.

In one illustrative embodiment of the invention, a polymeric network and/or any other support network for tissue engineering applications is spatially patterned with bioactive signals such as one or more D amino acid peptides. Suitable support materials for most tissue engineering applications are generally biocompatible and preferably biodegradable. Examples of suitable biocompatible and biodegradable supports include: natural polymeric carbohydrates and their synthetically modified, crosslinked, or substituted derivatives, such as agar, agarose, crosslinked alginic acid, chitin, substituted and cross-linked guar gums, cellulose esters, especially with nitric acid and carboxylic acids, mixed cellulose esters, and cellulose ethers; natural polymers containing nitrogen, such as proteins and derivatives, including crosslinked or modified gelatins, and keratins; vinyl polymers such as poly(ethylene glycol)acrylate/methacrylate, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a pre-existing natural polymer. A variety of biocompatible and biodegradable polymers are available for use in therapeutic applications; examples include: polycaprolactione, polyglycolide, polylactide, poly(lactic-co-glycolic acid) (PLGA), and poly-3-hydroxybutyrate. Methods for making nanoparticles from such materials are well-known.

In typical embodiments of the invention, a hydrogel is coupled to or patterned with a selected bioactive signal(s) in the present invention such as one or more peptides comprising at least one D amino acid. Hydrogels are networks of hydrophilic polymer chains that may be used as tissue culture systems that mimic the natural stem cell niche. Because hydrogels have mechanical properties similar to natural tissues and may be modified with natural ligands, hydrogels are good platforms for in vivo applications. Preferably, the gel is biocompatible and/or biodegradable. Hyaluronic acid, poly(ethylene glycol), and fibrin form suitable hydrogels. Hyaluronic acid-based hydrogels can be formed from hyaluronic acid engineered, e.g., with sulfhydryl groups undergoing Michael addition with MMP-sensitive peptide diacrylates.

In an illustrative embodiment, the hydrogel used in the present invention is a hyaluronic acid ("HA") hydrogel. For example, hyaluronic acid-acrylate ("HA-ACR") is used. HA is a linear disaccharide of D-glucuronate and D-N-acetylglucosamine with alternating $\beta$-1,4 and $\beta$-1,3 glycosidic bonds. HA is found in most organs and tissues, including skin, joints, and eyes (see, e.g., Almond A. Hyaluronan. Cell Mol Life Sci 2007 May 14). HA and hyaluronidase (Haase) degradation fragments have also been found to be important during embryonic development, tissue organization, angiogenesis and tumorigenesis (see, e.g., Rodgers L S, Lalani S, Hardy K M, Xiang X, Broka. D, Antin P B, et al. Depolymerized hyaluronan induces vascular endothelial growth factor, a negative regulator of developmental epithelial-to-mesenchymal transformation. Circ Res 2006 Sep. 15; 99(6): 583-589). HA is both actively synthesized and degraded into HA oligos during the initial stages of wound healing (see, e.g., Pogrel M A, Pham H D, Guntenhoner M, Stern R. Profile of hyaluronidase activity distinguishes carbon dioxide laser from scalpel wound healing. Ann Surg 1993 February; 217(2):196-200) and after stroke in man (Al'Qteishat A, Gaffney J, Krupinski J, Rubio F, West D, Kumar S, et al. Changes in hyaluronan production and metabolism following ischaemic stroke in man. Brain 2006 August; 129 (Pt 8):2158-2176). Further, HA hydrogels may promote hES stem cell renewal when unmodified with integrin binding ligands. Thus, differentiation will likely be the result of differentiation signals introduced into the scaffold. Accordingly, the HA hydrogel is an ideal scaffold to transplant cells into the brain after stroke and to aid in wound healing. HA hydrogels may promote hES stem cell renewal when unmodified with integrin binding ligands (see, e.g., Gerecht, S. et al. Hyaluronic acid hydrogel for controlled self-renewal and differentiation of human embryonic stem cells. *Proc Natl Acad Sci USA* 104, 11298-11303 (2007). As such, preferably, differentiation will be the result of signals introduced into the scaffold. Unlike poly(ethylene glycol) ("PEG"), the HA hydrogel may be customized to contain more sites of modification and/or cross-linking, and may be completely biodegradable.

In other embodiments, a PEG hydrogel may be used. For example, PEG hydrogel may be available as 2, 4, or 8 arm molecules and, thus, may provide a maximum of 8 sites for modification and/or crosslinking per molecule. (The HA hydrogel, however, may be modified to contain about 77 acrylate groups per molecule. Accordingly, it may provide at least 9 times more sites for modification and/or crosslinking. Preferably, having more sites available for modification/crosslinking results in a wider range of bioactive signal incorporation without compromising crosslinking density (i.e., mechanical properties). For example, with even 77 acrylates per chain (48% modification of the COOH groups in HA), HA hydrogels may be completely degradable by hyaluronidase). For example, PEG-vinyl sulfone ("PEG-VS") may be used. PEG is a synthetic polymer that is widely used in biomedical applications ranging from implant coatings to drug delivery and tissue engineering. Because PEG is biologically inert, it can serve as a blank slate to display bioactive signals and study their role in stem cell differentiation or renewal. Further, both HA and PEG polymers are highly hydrated in water and have low protein absorption to their backbone, which is ideal for the synthesis of biomaterials with a very defined composition. The synthetic approach used to crosslink HA and PEG polymers into hydrogels to allow for the encapsulation of stem cells. Thus, it may be done under close to pH=7.4, 4° C. to 37° C. temperature, and in aqueous buffers with 150 mM salt. For example, Michael addition of dithiol containing crosslinkers to vinyl groups present on HA or PEG may be used to crosslink the networks (see, e.g., Adelow C, Segura T, Hubbell J A, Frey P. The effect of enzymatically degradable poly(ethylene glycol) hydrogels on smooth muscle cell phenotype. Biomaterials 2008 January; 29(3):314-326). Prior to crosslinking, the HA-ACR or PEG-VS may be modified with integrin binding peptides such as RGD if no ECM proteins are to be incorporated and the K* peptide via Michael addition. In yet other embodiments, any hydrogel and/or hydrogel-based system may be used in the invention.

In typical embodiments of the invention, the hydrogels disclosed herein are immobilized with one or more bioactive signals. It is to be understood that one or more different bioactive signals may be immobilized within a single hydrogel. The bioactive signal may be linked with Q-peptide; however, it does not need to be. The bioactive signal(s) as disclosed herein may be a D-amino acid peptide that acts as an adjuvant (and/or immunogen) or in combination with one or more growth factors, extracellular matrix proteins, peptides, carbohydrates and/or a fragment(s) thereof. Optionally, the bioactive signal(s) in the present invention is RGD (or the Arg-Gly-Asp peptide). RGD is a bioactive adhesion motif found in the extracellular matrix (ECM) glycoprotein fibronectin.

In another illustrative embodiment, the bioactive signal may be one or more D amino acid peptides and peptide immunogens in combination with one or more agents know to modulate immune cells and/or wound healing such as growth factors. For example, the bioactive signal may be Q-VEGF and/or Q-PDGF (Q peptide with the respective growth factors). In yet other embodiments, the bioactive signal(s) does not contain the Q-peptide as disclosed herein. For example, the bioactive signal(s) may be immobilized without the use of the Q-peptide as disclosed herein, without departing from the scope of the present invention. In yet other embodiments, the bioactive signal may be protein fragments such as carbohydrates (i.e., heparin), small molecule drugs, and/or synthetic polymers and/or any extracellular matrix protein (i.e., collagen, fibronectin, laminin, vitronectin, and fibrin), peptide (i.e., adhesion moieties (RGD, IKVAV (SEQ ID NO: 5), antimicrobial peptides), carbohydrate (hyaluronic acid) or/or any fragment of thereof and/or any combination thereof.

In an illustrative embodiment, the biosignal(s) described herein may be attached to the substrate via solid phase synthesis (i.e., for peptide biosignals); via DNA cloning (i.e., for protein biosignals); via NHS-ester conjugation chemistry; thiol-ene conjugation chemistry and/or disulfide attachment.

In an illustrative embodiment, "Q peptide(s)" preferably refers to the peptide sequence NQEQVSPL (SEQ ID NO: 2) and/or sequences containing NQEQVSPL (SEQ ID NO: 2). The Q peptide is the sequence recognized by FXIIIa in plasminogen inhibitor α2P1 (see, e.g., Sakata Y, Aoki N. Cross-linking of alpha 2-plasmin inhibitor to fibrin by fibrin-stabilizing factor. J Clin Invest 1980 February; 65(2): 290-297). As used herein, "Q peptide-RGD" may refer to H-NQEQVSPLRGDSPG-NH$_2$ (SEQ ID NO: 3) and/or any other sequence having Q peptide as defined herein and having the sequence RGD. In other embodiments, Q peptide may refer to any peptide sequence having Q. Preferably, the Q peptide is linked to the bioactive signal(s). In other embodiments, the bioactive signal may be immobilized without the use of the Q-peptide.

In an illustrative embodiment, an enzyme that may cleave the selected substrate(s) to produce a site to which a bioactive signal is subsequently attached and/or to form a bond(s) between the selected substrate and the selected bioactive signal is used in the present invention. Preferably, the selected enzyme forms a bond between the selected substrate(s) and the selected bioactive signal(s). Preferably, the bond is a covalent bond. In other embodiments, the bond is not a covalent bond. It is to be understood that any enzyme that is capable of covalent bond formation and/or any other bond may be used. Preferably, the invention disclosed herein includes the use of any enzyme capable of covalent bond formation and the photoactive caging of one of two enzyme-recognized substrates that participate with said enzyme.

In an illustrative embodiment, the enzyme Factor XIIIa (or "FXIIIa") is used in the present invention. FXIIIa is a naturally-occurring transglutaminase enzyme that catalyzes the formation of a covalent bond between K and Q amino acids in proteins or peptides. Specifically, it catalyzes a transamination reaction between the second Q of the Q peptide described herein and the amine on the K peptide side chain to generate a non-canonical covalent bond between the Q and the K amino acid side chains. Preferably, this reaction is chemospecific. FXIIIa and the peptide NQEQVSPL (SEQ ID NO: 2) (derived from 2-plasmin inhibitor ($_2$-PI$_{1-8}$) (Schense, J. C.; Hubbell, J. A. *Bioconjug Chem* 1999, 10, 75) have been previously used to immobilize growth factors (see, e.g., Zisch A H, Schenk U, Schense J C, Sakiyama-Elbert S E, Hubbell J A. Covalently conjugated VEGF—fibrin matrices for endothelialization. J Control Release 2001 May 14; 72(1-3):101-113), protein fragments see, e.g., Martino M M, Mochizuki M, Rothenfluh D A, Rempel S A, Hubbell J A, Barker T H. Controlling integrin specificity and stem cell differentiation in 2D and 3D environments through regulation of fibronectin domain stability. Biomaterials 2009 February; 30(6):1089-1097) and peptides (see, e.g., Schense J C, Hubbell J A. Cross-linking exogenous bifunctional peptides into fibrin gels with factor XIIIa. Bioconjug Chem 1999 January-February; 10(1):75-81) to fibrin hydrogels through bulk modification. Further, FXIIIa has been used to catalyze the gelation of PEG to form a hydrogel (see, e.g., Ehrbar M, Rizzi S C, Schoenmakers R G, Miguel B S, Hubbell J A, Weber F E, et al. Biomolecular hydrogels formed and degraded via site-specific enzymatic reactions. Biomacromolecules 2007 October; 8(10):3000-3007; Hu, B. H.; Messersmith, P. B. *J Am Chem Soc* 2003, 125, 14298). In nature, this enzyme is active during the wound-healing cascade, where it stabilizes fibrin clots and introduces bioactive signals to the clot such as fibronectin, collagen, and laminin. In other embodiments, other enzymes may be used to catalyze a reaction and/or form a bond between the Q-peptide-RGD and the K peptide. In other embodiments, any other transglutamase enzyme may be used. For example, one or more of the following may be used in lieu of, or in connection with, FXIIIa: transglutamases 1-7 and/or any other enzyme capable of forming an amide bond between a lysine and a glutamine may be used. In yet other embodiments, any enzyme capable of catalyzing/forming covalent bonds may be used in lieu of, or in connection with, FXIIIa. For example, the bioactive signals disclosed herein may be covalently attached to an enzyme-recognized substrate via any method, including synthetic chemistry methods (i.e., peptide synthesis methods), DNA cloning, and conjugation chemistry.

In one aspect of the invention, an immune-modulating biomaterial is provided. The embodiment contains D-chirality peptides (either as a crosslinking peptide or as a chemically-attached chemical moiety). The presence of amino acids that are D-chirality (as opposed to the L-chirality commonly found in mammalian proteins) causes a significant and localized immune response. The size and physical geometry of the hydrogel is independent of the overall action, however in one or more embodiments, the reduction to practice was done using a hydrogel particle-based biomaterial.

In another aspect of the invention, a method for modulating an immune response is provided. The method comprises administering an immune-modulating biomaterial in vivo, wherein the biomaterial comprises a hydrogel scaffold comprising a D-chirality peptide. In certain instances, the method of modulating an immune response results in an increased or amplified immune response (e.g. as shown in FIG. 7).

In one or more embodiments of the invention, the D-chirality peptide is a crosslinker forming part of a backbone structure of the hydrogel scaffold. In other embodiments, the D-chirality peptide is a peptide sequence attached to a backbone structure of the hydrogel scaffold. In one instance the D-chirality peptide has an amino acid sequence of Gly Cys Arg Asp Gly Pro d-Gln Gly d-Ile d-Trp Gly Gln Asp Arg Cys Gly (SEQ ID NO: 6), wherein "d-Xxx" denotes an amino acid with D-chirality. In various embodiments, the D-chirality peptide is attached to the backbone structure covalently or non-covalently, for example through Michael addition, pseudo-Michael addition, radical polymerization of a vinyl group, or an ionic bond.

FIG. 1 illustrates D-chirality amino acid incorporation into a hydrogel, in accordance with one or more embodiments of the invention. The D-chirality amino acids can be incorporated as either a crosslinker that becomes part of the hydrogel backbone structure (indicated with arrow A) or as a covalently or non-covalently backbone-attached peptide sequence (indicated with arrow B). In one or more embodiments, the D crosslinker has a sequence of {GLY}{CYS}{ARG}{ASP}{GLY}{PRO}{d-GLN}{GLY}{d-ILE}{d-TRP}{GLY}{GLN}{ASP}{ARG}{CYS}{GLY} (SEQ ID NO: 6), wherein the D-chirality amino acids are denoted as {d-XXX}. In one or more embodiments, chemistries for linking the D peptide to the backbone polymer include: Michael or pseudo-Michael addition (nucleophilic addition of carbanion or nucleophile to an unsaturated carbonyl) and radical polymerization of a vinyl group for covalent attachment. In other embodiments, ionic bonding (positive to negative charge) is used for non-covalent attachment.

Although the invention is not limited to any specific theory or mechanism, different possible theories have been contemplated for the observed modulated (e.g. increased) immune response. Under one theory, neutrophils and macrophages are responding via an innate response to the unnatural chirality of the peptides. Under a second theory, an adaptive T-cell mediated immune response is targeting the specific sequence of the D-amino acid containing peptide.

One advantage for using the biomaterial provided herein to modulate an immune system response in a beneficial manner (e.g. improve healing, eliminate malignant cancers, etc.) is the extended exposure the solid material has relative to liquid solutions (which are quickly cleared and eliminated from the body through the urinary tract). In addition, biomaterial-based approaches can either be localized to the tissue or systemically delivered. Immune modulation with the biomaterial allows for more natural wound regeneration. This also allows for new approaches to vaccination and cancer treatment. Currently in the art, the methods for immune modulation disclosed herein are the only examples of peptide chirality being used to control tissue behavior in biomaterials (represents a clear non-obvious deviation from current synthetic and natural biomaterials). There is no knowledge of other hydrogels or materials in the art that use D-chirality amino acids for any intended purpose in vivo.

Embodiments of the invention can use a microfluidic water-in-oil emulsion approach to segment a continuous pre-gel aqueous phase into uniform scaffold building blocks. Generating microgel building blocks serially at the microscale, rather than using typical vortex and sonication-based approaches allows tight control over the formation environment and ultimate material properties of the emergent MAP gel. By tuning the flow rates of both the pre-gel solution and the pinching oil flow, as well as the geometry of the microfluidic channel, artisans can create a range of microgel sizes with low polydispersity. Fabrication methods can be serial yet retain practicality in its high-throughput nature, with generation rates that ranged from 250 Hz for larger particles (>100 μm) to 1,200 Hz for small particles (~15 μm). This translates to roughly 100 μl of pre-swollen gel every 50 min for a single device. This approach ultimately resulted in particles that were highly monodisperse, both physically and chemically.

Illustrative microgel building blocks can be composed of a completely synthetic hydrogel mesh of multi-armed poly (ethylene) glycol_vinyl sulphone (PEG-VS) backbones decorated with cell adhesive peptide (RGD) and transglutaminase peptide substrates (K and Q). The microgels can be crosslinked via Michael-type addition with cysteine-terminated matrix metalloprotease-sensitive peptide sequences that allow cell controlled material degradation and subsequent resorption. The microgel building blocks can be purified into an aqueous solution of isotonic cell culture media for storage.

The microgel building blocks can be annealed to one another to form a MAP gel via a non-canonical amide linkage between the K and Q peptides mediated by activated Factor XIII (FXIIIa), a naturally occurring enzyme responsible for stabilizing blood clots. This enzyme-mediated annealing process allows incorporation of living cells into a dynamically forming MAP scaffold that contained interconnected microporous networks. Following addition of FXIIIa, but before scaffold annealing, a slurry of the microgel building blocks can be delivered via syringe application, ultimately solidifying in the shape of the area into which they are injected. Structural changes leading to an increase in storage modulus in the annealed gels is observed on addition of FXIIIa to the microgel building blocks. Microgel annealing was necessary for scaffold formation via high-vacuum SEM observation, wherein on dehydration the scaffolds adopted a highly stretched but interconnected mesh, whereas building blocks without FXIIIa can be separated into individual spherical beads. By tuning the microgel building-block size and composition artisans can generate a diverse set of assembled MAP scaffolds.

By using building-block sizes from 30 to 150 μm in diameter, artisans can achieve networks with median pore diameters ranging from ~1 to ~50 μm (e.g. ~10 to ~35 μm). Different PEG weight percentages and crosslinker stoichiometries can provide a range of easily achievable building-block storage moduli from ~10 to 1,000 Pa, which spans the stiffness regime necessary for mammalian soft tissue mimetics. Physically matched MAP and non-porous gels demonstrated differential degradation kinetics when exposed to a protease cocktail in vitro, indicating greater access of the protease to MMP-cleavable sites within the MAP gel due to its microscale porosity.

The hydrogels can be prepared using a published technique (Griffin et al., "Accelerated Wound Healing by Injectable Microporous Gel Scaffolds Assembled from Annealed Building Blocks." *Nature Materials* 2015 July; 14(7):737-44, the contents of which are incorporated herein by reference). Illustrative but non-limiting methods and materials that can be used to make embodiments of the invention are disclosed in the text immediately below. Further aspects and embodiments of the invention are disclosed in the following example.

Example Methods and Materials Useful to Practice Embodiments of the Invention

Microfluidic Device Design and Fabrication

Microfluidic water-in-oil droplet generators can be fabricated using soft lithography using conventional technologies. Briefly, master molds can be fabricated on mechanical grade silicon wafers (University wafer) Using KMPR 1025 or 1050 photoresist (Microchem). Varying channel heights can be obtained by spinning photoresist at different speeds, per the manufacturer's suggestions. Devices can be molded from the masters using poly(dimethyl)siloxane (PDMS) Sylgard 184 kit (Dow Corning). The base and crosslinker can be mixed at a 10:1 mass ratio, poured over the mold, and degassed prior to curing for 6 hours at 65° C. Channels can be sealed by treating the PDMS mold and a glass microscope slide (VWR) with oxygen plasma at 500 mTorr and 75 W for 15 seconds. Immediately after channel sealing, the channels can be functionalized by injecting 100 μl of a solution of Rain-X and reacting for 20 mins at room temperature. The channels can be then dried by air followed by desiccation overnight.

Microfluidic Building Block Generation Using Droplet Segmentation

Droplets can be generated using a microfluidic water-in-oil segmentation system. The aqueous phase can be a 1:1 volume mixture of two parts: (i) a 10% w/v PEG-VS (20 kDa) in 300 mM triethanolamine (Sigma), pH 8.25, pre-functionalized with 500 μM K-peptide (Ac-FKGGERCG-NH2) (SEQ ID NO: 1) (Genscript), 500 μM Q-peptide (Ac-NQEQVSPLGGERCG-NH2) (SEQ ID NO: 2), and 1 mM RGD (Ac-RGDSPGERCG-NH2) (SEQ ID NO: 7) (Genscript) and (ii) an 8 mM di-cysteine modified Matrix Metallo-protease (MMP) (Ac-GCRDGPQGIWGQDRCG-NH2) (SEQ ID NO: 8) (Genscript) substrate pre-reacted with 10 μM Alexa-fluor 647-maleimide (Life Technologies).

All solutions can be sterile-filtered through a 0.2 μm Polyethersulfone (PES) membrane in a leur-lok syringe filter. Generation can be performed at 37° C. on an incubated microscope stage (Nikon eclipse Ti) for real time monitoring of μgel quality. Aqueous solutions typically do not mix until droplet segmentation (Peclet number>10). The oil phase can be a heavy mineral (Fisher) oil supplemented with 0.25% v/v Span-80 (Sigma). Downstream of the segmentation region, a second oil inlet with a high concentration of Span-80 (5% v/v) can be added and mixed to the flowing droplet emulsion. Ultimately, the μgel-in-oil mixture can be exited into a large (12 mm diameter, ~1 mL volume) well, where the μgels cured at 37° C. for a minimum of 1 hour. The mixture can be then extracted and purified by overlaying the oil solution onto an aqueous buffer of HEPES buffered saline pH 7.4 and pelleting in a table top centrifuge at 18000×g for 5 mins. The μgel pellet can be washed in HEPES buffered saline pH 7.4 with 10 nM CaCl2 and 0.01% w/v Plutonic F-127 (Sigma). The μgel aqueous solution can be then allowed to swell and equilibrate with buffer for at least 2 hours at 37° C.

Microfluidic Operational Regime Characterization

To determine the operational regime of droplet segmentation, artisans can monitor device operation in real time using a high-speed camera (Phantom), followed by image analysis for size and polydispersity measurement (ImageJ) as well as segmentation frequency (Phantom PC2). For stable droplet segmentation on this platform: (i) initiate all flows simultaneously (both aqueous flows and both oil flows) at 5 μl/min until all air has been flushed from the device, (ii) turn down aqueous flow rates to the desired overall volumetric rate and flow for 5 mins, (iii) aspirate all accumulated liquid from collection well to ensure collection of monodisperse μgels, and (iv) run generation.

Generation of MAP Scaffolds from Building Block μgels

Fully swollen and equilibrated building block μgels can be pelleted at 18000×g for five minutes, and the excess buffer (HEPES pH 7.4+10 mM CaCl2) can be removed by aspiration and drying with a cleanroom wipe. Subsequently, building blocks can be split into aliquots, each containing 50 μl of concentrated building blocks. An equal volume of HEPES pH 7.4+10 mM CaCl2 can be added to the concentrated building block solutions. Half of these can be spiked with Thrombin (Sigma) to a final concentration of 2 U/ml and the other half spiked with FXIII (CSL Behring) to a final concentration of 10 U/ml. These solutions can be then well mixed and spun down at 18000×g, followed by removal of excess liquid with a cleanroom wipe (American Cleanstat). Annealing can be initiated by mixing equal volumes of the building block solutions containing Thrombin and FXIII using a positive displacement pipet (Gilson). These solutions can be well mixed by pipetting up and down, repeatedly, in conjunction with stirring using the pipet tip. The mixed solution can be then pipetted into the desired location (mold, well plate, mouse wound, etc.).

Rheology Technique for Gelation Kinetics

To determine the gelation kinetics for each μgel, a macroscale (50 μL) non-porous gel can be generated with the same chemical composition. A 30 μL solution of 2×PEG-VS+peptides (RGD, K, and Q peptides) dissolved in 0.3 M TEOA can be combined with 30 μL of 2×MMP-1 crosslinker dissolved in water. The mixture can be quickly vortexed and 50 mL of the mixture can be placed between two 8 mm rheological discs at a spacing of 1 mm (Anton paar physica mcr 301 Rheometer). The storage modulus can be then measured over a period of 20 minutes (2.5 Hz, 0.1% strain).

Rheology Technique for MAP Gel Measurement

To determine the bulk storage modulus of the pre-annealed MAP building blocks and post-annealed MAP scaffold artisans can perform an amplitude sweep (0.01-10% strain) to find the linear amplitude range for each. An amplitude within the linear range can be chosen to run a frequency sweep (0.5-5 Hz). For pre-annealed building blocks, 50 μL of MAP building blocks (5 wt % PEG-VS, r=0.8 MMP-1 crosslinker, 250 mM K, 250 mM Q, 500 mM RGD) can be injected between two 8 mm rheological discs at a spacing of 1 mm. For post-annealed scaffold measurement, one can first pipette 50 μL of MAP building blocks (N=3) (5 wt % PEG-VS, r=0.8 MMP-1 crosslinker, 250 mM K, 250 mM Q, 500 mM RGD) spiked with FXIIIa, 5 U/mL final concentration, and thrombin, 1 U/mL final concentration, between two glass slides. This mixture can be allowed to partially anneal for 10 minutes before removal of top glass slide and placement in a humidified incubator at 37° C. for 90 minutes. The scaffolds can be then placed into HEPES buffered saline (pH 7.4) overnight to reach equilibrium. The samples can be then placed between two 8 mm discs on the rheometer and tested identically to the pre-annealed MAP building blocks.

MAP Scaffold Pore Size Measurement

To determine median pore size in the annealed MAP scaffolds, stock solutions of different sized building blocks can be used to anneal three separate MAP scaffolds from each (9 scaffolds in total). Using a Nikon Ti eclipse, equipped with C2 laser LED excitation, 10 z-slices can be taken in each gel, spanning a total of 500 um depth. These images can be then analyzed using a custom script written in Matlab, to identify the pore regions and calculate each one's size in px2. Each individual pore's size can be then used to calculate the median pore size for that gel, and converted to $\mu m^2$ using the pixel to μm conversion from the original microscope image (0.31 μm/px). These areas can be then converted to a characteristic length measurement by forcing the areas to a circle, and calculating the characteristic diameter of these circles.

Gel Degradation Experiments

To measure the degradation profiles of MAP and non-porous gels, equal volumes of MAP and the non-porous counterpart can be pipetted into the corner of a 96-wel plate, and gelled in this orientation. The MAP gels can be comprised of 100 μm diameter (after swelling) μgels containing 5% wt 4 arm PEG-VS, 8 mM MMP crosslinker, 250 μM K peptide, 250 μM Q Peptide, 500 μM RGD peptide, and 10 μM alexa fluor 647 maleimide. The non-porous gels contained 4.5% wt 4-arm PEG-VS, 7.2 mM MMP crosslinker, 250 μM K peptide, 250 μM Q peptide, 500 μM RGD peptide, and 10 μM alexa fluor 647 maleimide.

After gelation for 90 mins at 37° C., the MAP and non-porous gels can be rehydrated in HEPES pH 7.4 for 2 hours at 37° C. Subsequently, the gels can be exposed to 100 μl of a 1:1000 dilution of TripLE (Invitrogen) in HEPES pH 7.4. The well plate can be rotated at 150 rpm in a 37° C. shaker. At 30 min intervals, 5 μl of supernatant can be removed, diluted 1:2 in HEPES pH 7.4, and this 10 μl solution can be plated in a black-walled, clear bottom 384 well plate (Greiner Bio). After all time points can be collected, the solution fluorescence can be measured in a Biotek Synergy microplate reader (Ex: 635, Em: 665). This raw fluorescence can be measured against an on-plate calibration curve of alexa fluor 647 maleimide and plotted as % degradation over time.

Scanning Electron Microscopy (SEM) of MAP Scaffolds

To determine if μgel building blocks can be covalently linked after addition of FXIIIa, SEM can be used to directly visualize scaffolds. Building block mixtures can be either treated with FXIIIa (10 U/ml) or with buffer only. Subsequently, the building block solutions can be placed onto a 1×1 in silicon wafer piece, and dried in an SEM (Hitachi S4700) high vac chamber (1×10−3 mTorr). Building blocks with or without FXIIIa can be then visualized using 10 kV (10 mA max) on either 200× or 500×.

Cell Culture:

HEK293T cells constitutively expressing GFP via lentiviral transfection can be maintained in DMEM (Life Technologies) supplemented with 10 μg/ml puromycin. Three cell lines can be used for typical in vitro experiments: human dermal fibroblasts (HDF, Life Technologies), bone marrow-derived human mesenchymal stem cells (BMhMSC, Life Technologies), and adipose-derived human mesenchymal stem cells (AhMSC, Life Technologies). All cell lines can be maintained according to manufacturer's specifications (before and after incorporation into MAP or non-porous gels). Specifically, for the MSC populations reduced-serum, basal medium (Life Technologies) can be used to retain stemness.

Cell Incorporation into MAP Scaffolds and Subsequent In Vitro Culture

For quantification of cell proliferation and visualizations of network formation in MAP scaffolds in vitro, MAP scaffolds can be annealed for μgel building blocks as described above, with the addition of cell suspensions to the building block solutions prior to annealing. For each cell line, cell suspensions can be prepared at a final concentration of 25×106 cells/ml in respective culture media unsupplemented with serum. Subsequently, 2 μl of cell suspension can be added to 50 μl of building block mixture containing FXIII and combined with 50 μl of building block mixture containing Thrombin (500 cells/μl of gel). This mixture can be injected into the corner of a coverslip-bottom PDMS well. The well top can be covered with a second coverslip and the μgel/cell mixture can be allowed to undergo annealing for 90 minutes at 37° C.

After annealing can be completed, the top coverslip can be removed, and the appropriate complete culture media can be added to the PDMS well. For the day 0 time point, 4% PFA can be added directly to the PDMS wells and allowed to fix overnight at 4° C. Other cells can be grown in 5% CO2 and 37° C. for the times indicated (2, 4, and 6 days), at which point they can be washed once with 1×PBS and fixed with 4% PFA overnight at 4° C. HEK-293-T cells can be incorporated into the star mold by mixing cells with MAP building blocks (as described above) and pipetting 5 μl of the mixture into the center of the mold. Immediately following, MAP building blocks without cells can be pipetted in the remainder of the mold, and annealed as described above.

Figure 3A:
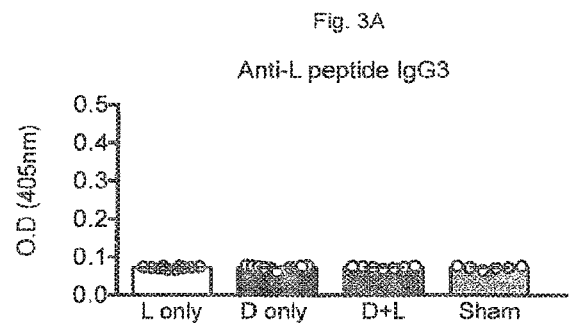
FIGS. 3A-3F show data from experiments where different microporous annealed particle (MAP) D and/or L peptide compositions were injected into mice and the resultant antibody response (antibody classes IgG1, IgG2a and IgG3) measured by ELISA.
Figure 3B:
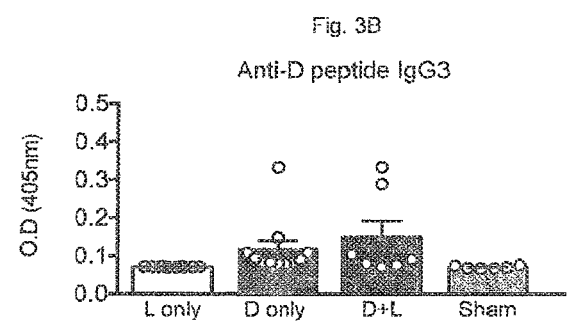
Figure 3C:
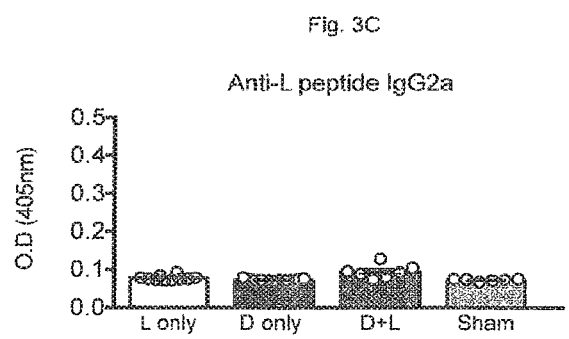
Figure 3D:
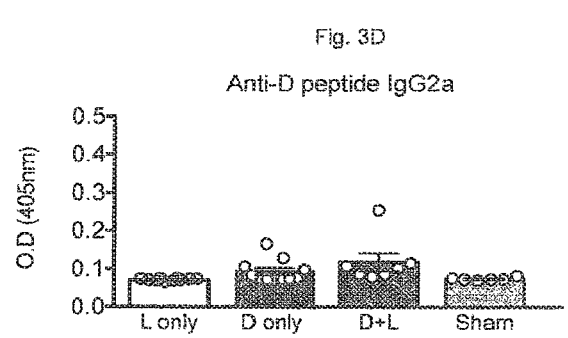
Figure 3E:
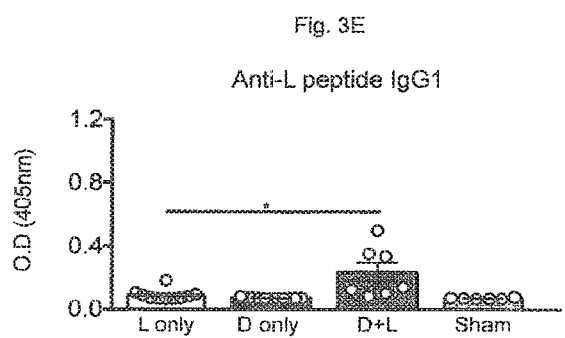
Figure 3F:
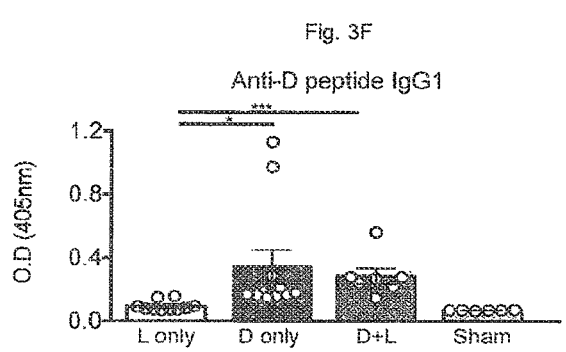

Proliferation can be assessed by counting the number of cell nuclei present in the MAP scaffold constructs after 0, 2, 4, and 6 days of culture in vitro. Nuclei can be stained with a 2 μg/ml DAPI solution in 1×PBS for 2 hours, followed by visualization on a Nikon C2 using the 405 nm LED laser. Specifically, each scaffold can be imaged by taking 55 z slices in a 150 μm total z height and compressing every 5 slices into a maximum intensity projection (MIP) image. Nuclei in the MIPs can be enumerated using a custom Matlab script, counting the total number of cells. For each time point, z-stack images of three separate MAP scaffolds can be analyzed, where each z-stack image measured a total volume of 1270×1270×150 μm3 (or ~280 nL). The day 0 counts from FIG. 3d lead to a calculation of ~525 cells/μl of gel, consistent with the experimental amount added (500 cells/μl of gel).

For visualization of cell network formation within the MAP scaffolds in vitro, the constructs can be prepared, grown, and fixed as above. The scaffolds can be blocked with 1% BSA in 1×PBS for 1 hour at room temperature, followed by staining for f-actin via an Rhodamine-B conjugate of phalloidin (Life Technologies) for 3 hours at room temperature. The scaffolds can be then washed with 1% BSA in 1×PBS, followed by counterstaining with a 2 μg/ml DAPI solution in 1×PBS for 1 hour at room temperature. Imaging can be performed as with proliferation imaging, with the exception of using a 40× magnification water immersion lens. Total heights of image stacks can be 130 µm, with the total number of slices at 260 (volume captures ~15 nL).

Non-Porous Cell Proliferation

PEG-VS scaffolds (5 wt % r=0.8 MMP-1 crosslinker, 250 µM K, 250 µM Q, 500 µM RGD) can be used to encapsulate cells (500 cells/µL). Cell lines used can be the same as in MAP scaffold experiments. Gels can be formed for 20 minutes (TEOA 0.3 M, pH 8.25) before being placed into appropriate media. The gels can be fixed after pre-determined time points (t=90 minutes, 2 days, 4 days, and 6 days) using PFA overnight at 4° C., washed and stored in PBS. Gels can be stained as in the MAP scaffolds. All samples can be stored at 4° C. in PBS with P/S when not being imaged. Imaging can be performed using a Nikon C2 confocal exactly as in the MAP scaffold in vitro experiments.

General Surgical Technique for Skin Wound Healing

Mouse excisional wound healing model Mouse excisional wound healing experiments can be performed based on a published protocol for biasing murine skin wound closure in favor of cutaneous regeneration by preventing wound contraction. Sample size for CLR:Skh1-Hrhr can be determined using power analysis for measurement of continuous variables. For a significance level ($\alpha$) greater than 95% ($\alpha$=0.05) and a power (1–$\beta$) greater than 0.9, we required an N of 6 per condition based on previous example. Sample size for BALB/c can be determined using power analysis for measurement of continuous variables. For a significance level ($\alpha$) greater than 95% ($\alpha$=0.05) and a power (1–$\beta$) greater than 0.9, we required an N of 5 per condition based on our pilot experiment in CLR:Skh1-Hrhr. Balb/c mice (Charles River Laboratories) can be anesthetized using continuous application of aerosolized isofluorane (1.5 vol %) throughout the duration of the procedure. The dorsal and side skin can be dehaired using a combination of electric clippers and Nair (Church and Dwight, Inc.) exposure (this step can be skipped for the CLR:Skh1-Hrhr mice) and disinfected with serial wash of povidone-iodine and 70% ethanol. The nails can be trimmed to lower the incidence of splint removal. The mice can be placed on their side and dorsal skin can be pinched along the midline. A sterile 4 mm biopsy punch can be then used to create two clean-cut, symmetrical, full-thickness excisional wounds on either side of the dorsal midline. A small amount of adhesive (VetBond, 3M, Inc.) can be then applied to one side of a rubber splint (O.D. ~12 mm; I.D. ~8 mm) and the splint can be placed centered around the wound (adhesive side down). The splint can be secured with eight interrupted sutures of 5-0 non-absorbable prolene. A second splint wrapped in Tegaderm (3M, Inc.) can be attached to the initial splint via a single suture to act as a hinged cover to allow wound imaging while acting as a physical barrier above the wound bed. The experimental material can be then added to the wound bed as follows:

A: MAP gel (5 wt %, r=0.8, 500 µM RGD, 250 µM K, 250 µM Q, 10 µM Alexa fluor maleimide)—12 µL of MAP in HEPES-buffered saline (pH 7.4) containing FXIII (10 U/mL) and 10 mM CaCl2 can be combined as mixed thoroughly with 12 µL of MAP in HEPES-buffered saline (pH 7.4) containing thrombin (2 U/mL) and 10 mM CaCl2 with a positive displacement pipette (MICROMAN, Gilson, Inc.). 20 µL of this mixture can be added into the wound bed by positive displacement pipette and allowed to anneal for 10 minutes. (e.g. Used for both mouse strains)

B: Chemically-matched non-porous control (5 wt %, r=0.8, 500 µM RGD, 250 µM K, 250 µM Q)—12 µL of PEG solution (10 wt %, 1000 µM RGD, 500 µM K, 500 µM Q in 0.3 mM triethanolamine, pH 8.8) can be combined and thoroughly mixed with 10.8 µL of crosslinker solution (8 mM MMP crosslinker, 10 µM Alexa fluor maleimide in DI water) and 1.2 µL of premixed factor XIII/thrombin (50 U/mL FXIII and 10 U/mL thrombin HEPES-buffered saline pH 7.4 with 10 mM CaCl2, kept at 4° C. to minimize pre-injection activation). 20 µL of the mixture can be added to the wound bed and allowed to gel for 10 minutes. (e.g. Used for CLR:Skh1-Hrhr mouse strain)

C: Physically-matched non-porous control (4.5 wt %, r=0.8, 500 µM RGD, 250 µM K, 250 µM Q)—12 µL of PEG solution (9 wt %, 1000 µM RGD, 500 µM K, 500 µM Q in 0.3 mM triethanolamine, pH 8.8) can be combined and thoroughly mixed with 10.8 µL of crosslinker solution (7.2 mM MMP crosslinker, 10 µM Alexa fluor maleimide in DI water) and 1.2 µL of premixed factor XIII/thrombin (50 U/mL FXIII and 10 U/mL thrombin in HEPES-buffered saline pH 7.4 with 10 mM CaCl2, kept at 4° C. to minimize pre-injection activation). 20 µL of the mixture can be added to the wound bed and allowed to gel for 10 minutes. (e.g. Used for BALB/c mouse strain)

D: Pre-cast PEG porous gel (5.5 wt %, r=0.8, 500 µM RGD, 250 µM K, 250 µM Q, 10 µM Alexa fluor maleimide)—An 5 mm disc can be cut from a 8 mm swollen disc (buffer: HEPES-buffered saline (pH 7.4) containing 10 mM CaCl2) using a 5 mm biopsy punch (wounds can be typically 5 mm in diameter after suturing to splint). 1.2 µL of premixed factor XIII/thrombin (50 U/mL FXIII and 10 U/mL thrombin in HEPES-buffered saline pH 7.4 with 10 mM CaCl2, kept at 4° C. to minimize pre-injection activation) can be added into the wound bed followed by placement of the pre-cast PEG porous gel into the center of the wound bed. The gels can be allowed to anneal to the surrounding tissue via FXIIIa for 10 minutes. (e.g. Used for BALB/c mouse strain)

E: Non-annealing µgels (5 wt %, r=0.8, 500 µM RGD, 0 µM K, 0 µM Q, 10 µM Alexa fluor maleimide 555)—12 µL of µgels in HEPES-buffered saline (pH 7.4) containing FXIII (10 U/mL) and 10 mM CaCl2 can be combined as mixed thoroughly with 12 µL of µgels in HEPES-buffered saline (pH 7.4) containing thrombin (2 U/mL) and 10 mM CaCl2 with a positive displacement pipette (MICROMAN, Gilson, Inc.). 20 µL of this mixture can be added into the wound bed by positive displacement pipette and allowed to sit for 10 minutes. (Used for BALB/c mouse strain)

F: No treatment—Nothing can be added to the wound bed for this control group. (e.g. Used for BALB/c mouse strain)

Treatment pairing for each mouse can be randomized. Following treatment wounds can be imaged using a digital camera, followed by closure of the Tegaderm-coated splint and wrapping of the wound sites using a self-adhering elastic bandage (VetWrap, 3M, Inc.). Animals can be housed individually to prevent wound and bandage abuse. The mice can be imaged at either days 1, 2, 4, and 5 (for CLR:Skh1-Hrhr mouse strain), or at days 5 and 7 (for BALB/c mouse strain). Digital imaging can be enabled by anesthetizing with isofluorane (1.5 vol %), removal of self-adhering elastic bandage, and lifting of tegaderm-coated splint. Following imaging the animals can be re-wrapped. At the culmination of the wound healing experiment (Day 1 or 5 for CLR:Skh1-Hrhr mouse strain and Day 7 for BALB/c mouse strain) the mice can be sacrificed by isofluorane overdose and cervical dislocation. The skin samples (CLR:Skh1-Hrhr mouse strain) can be retrieved and processed via either paraffin embedding for H&E staining (Day 1 CLR:Skh1-Hrhr mouse strain time point) or cryosectioning (Day 5 CLR:Skh1-Hrhr mouse strain time point).

Pre-cast porous PEG gels: Using a 6 mm biopsy punch a solid rectangle of PDMS (~5 mm×~500 mm×~200 mm) can be turned into a mold for PMMA bead casting. 50 mg of PMMA beads (53-63 µm in size, Cospheric) can be weighed and placed into each 6 mm well in the PMMA rectangle. The PMMA beads can be sintered together at 150° C. for 18 h. The mold can be then cooled to 4° C. before placing 16 µl of gelling PEG solution on top (5.5 wt % PEG-VS 4-arm 20 kDa, 500 µM RGD, 250 µM K, 250 µM Q, 20 µM Alexa fluor 647 maleimide). The mold can be then centrifuged at 500 g for 10 minutes at 4° C. to disperse the gelling solution between the sintered PMMA beads. The mold can be then placed at 37° C. for 90 minutes to reach complete gelation. Each gel-PMMA construct can be then placed into 100 mL of glacial acetic acid (Fisher) with 0.05% pluronic F-127 and agitated for 48 hours with two acid exchanges (100 mL after ~24 h and 36 h). The resultant leached precast porous PEG gels can be then placed into 50 mL of PBS (pH 7.4) with 0.05% pluronic F-127. The PBS solution can be exchanged after 2 hours with PBS with penicillin/streptomycin (0.1%) and kept at 4° C. either testing or implantation. The same batch of precast porous hydrogels used for in vivo experimentation can be tested by rheology (Anton paar physica mcr 301 Rheometer, 0.1% strain, 0.1-10 Hz) prior to implantation to ensure approximate physical matching to MAP gel (5.5 wt % precast: ~320 Pa).

CLR:SKH1-Hrhr Mice (Charles River Laboratories) (N=6 per test) can be anesthetized with isofluorane (1.5% for 10 minutes), followed by clipping of nails and injection of painkiller (buprenorphine, 60 µL per 20 g at 0.015 µg/µL). The skin can be pulled taut and a 4 mm biopsy punch can be used to create identical circular wounds on the back of the mouse. The periphery of the wounds can be secured using a rubber splint sewn via 7-8 stitches to the surrounding skin to prevent wound closure by contraction. Either non-porous (left side) or MAP (right side) hydrogel including 10 U/ml FXIII and 2 U/ml thrombin can be injected into wound beds, allowed to undergo gelation for 10 minutes, followed by subsequent covering of the wound by a stretchy gauze wrap to prevent animal interaction. The mice can be then separated into individual cages. Pain medication can be administered subcutaneously every 12 hours for the next 48 hours (for Day 1 sacrifices pain killer can be administered once after surgery).

Evaluation of Seamless Boundary, Cell Infiltration, and Immune Response at Day 1

At Day 1, mice (N=6) can be sacrificed via isofluorane overdosing, followed by subsequent spinal dislocation. The skin of the back can be removed using surgical scissors and the wound site can be isolated via a 10 mm biopsy punch. The samples can be immediately fixed using 4% formaldehyde at 4° C. (overnight) followed by transfer to ethanol and embedding of the sample into a paraffin block. The blocks can be then sectioned at 6 µm thickness by microtome (Leica) and underwent Hematoxylin and Eosin (H&E) staining. For quantification of cell infiltration within the hydrogels and immune response surrounding the hydrogels, a series of 3 random high power (40×) fields (HPFs) can be examined for each section. Samples can be analyzed for cell infiltration (>0.1 mm into the gel) by counting the total number of cells of any type within the injected hydrogels (N=6 with a sum of cells in 3 sections analyzed per wound). Greater than 95% of the cells infiltrating the gels can be neutrophils. To measure immune response, the average of 3 HPFs from different sections of the wound can be examined. The total number of leukocytes/HPF within 0.2 mm of the hydrogel at the wound edge can be quantified and averaged for each wound type. The leukocyte count for each wound can be compared to its bilateral control on the same animal and the relative difference can be recorded as a fraction of each animal's overall immune response. This comparison can be possible because each animal had one wound injected with the MAP scaffold and one wound with the non-porous control.

Evaluation of Wound Closure

Wounds can be imaged daily to follow closure of the wounds. Each wound site can be imaged using high-resolution camera (Nikon Coolpix). Closure fraction can be determined by comparing the pixel area of the wound to the pixel area within the 10 mm center hole of the red rubber splint. Closure fractions can be normalized to Day 0 for each mouse/scaffold type. Investigators can be blinded to treatment group identity during analysis.

Tissue Collection at Day 5 (CLR:SKH1Hrhr Only)

At Day 5, mice (N=6) can be sacrificed and tissue collected as in day 1 mice. The samples can be immediately submerged in Tissue-tek Optimal Cutting Temperature (OCT) fluid and frozen into a solid block with liquid nitrogen. The blocks can be then cryo-sectioned at 25 µm thickness by cryostat microtome (Leica) and kept frozen until use. The sections can be then fixed with 4% paraformaldehyde in 1×PBS for 30 minutes at room temperature, washed with 1×PBS, and kept at 4° C. until stained.

Tissue Section Immunofluorescence

Slides containing tissue sections can be either blocked with 3% normal goat serum (NGS) in 1×PBS+0.05% Tween-20 (PBST) or simultaneously blocked and permeabilized with 0.2% Triton X-100 in 5% Normal Goat Serum (NGS) or 10% Normal Donkey Serum (NDS) in 1×PBST for sections stained with anti keratin-5 only. Sections can be then washed in 3% NGS in 1×PBST. Primary antibody dilutions can be prepared as follows in 5% NGS or 10% NDS in 1×PBST: rat anti mouse CD11b clone M1-70 (BD Pharmingen; #553308)—1:100 rat anti mouse PECAM-1 clone 390 (BD Pharmingen; #558736)—1:100 rabbit anti mouse NG2 (Millipore; # AB5320)—1:100 goat anti human PDGFRβ (Abcam, Inc.; # ab10848) 1:200 chicken anti mouse keratin 5 (Covance, Inc.; # SIG-3475)—1:400 rabbit anti mouse keratin 14 (Covance, Inc.; # PRB-155P) 1:400 rat anti mouse CD49f (BioLegend; #313602) 1:250 Sections can be stained with primary antibodies overnight at 4° C., and subsequently washed with 3% NGS in 1×PBST. Secondary antibodies can be all prepared in 5% Normal Goat Serum (NGS) or 10% Normal Donkey Serum (NDS) in 1×PBST at a dilution of 1:250. Sections can be incubated in secondary antibodies for 1 hour at room temperature, and subsequently washed with 1×PBST. Sections can be counterstained with 2 µg/ml DAPI in 1×PBST for 30 mins at room temperature. Sections can be mounted in Antifade Gold mounting medium.

Illustrative Working Embodiments of the Invention

Figure 2A:
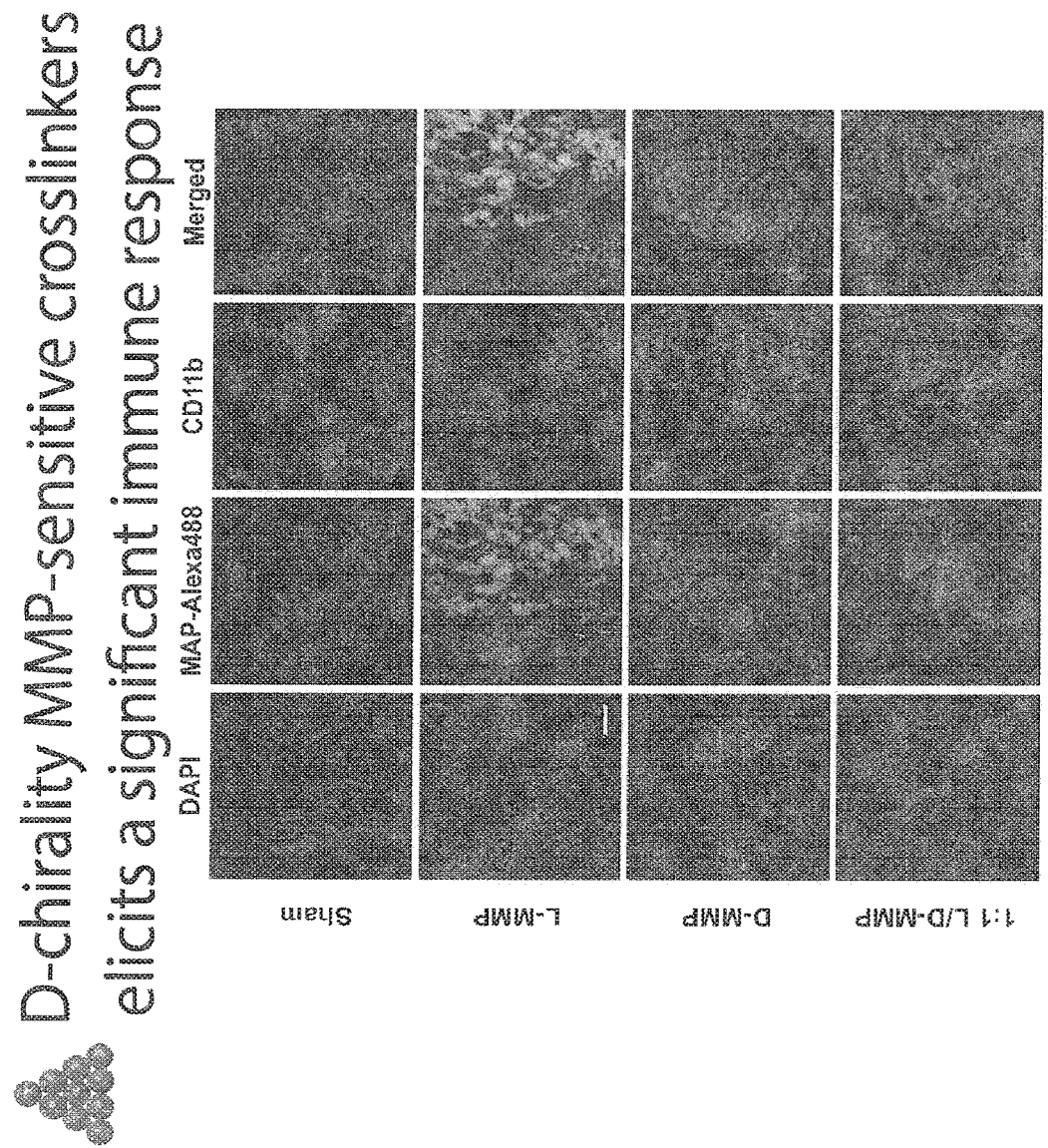
FIGS. 2A-2B show data from experiments where microporous annealed particle (MAP) compositions were injected into a skin wound environment, in accordance with one or more embodiments of the invention. 20 µl of PEG-based MAP microbeads were injected and the tissue was retrieved 21 days after application.
Figure 2B:
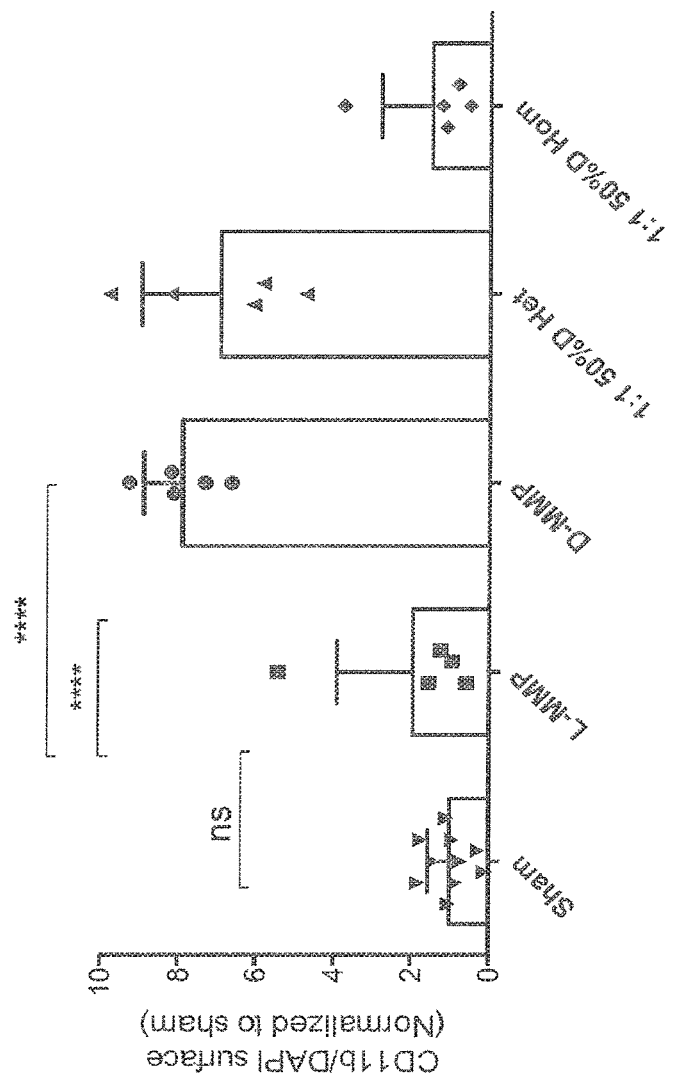
Figure 2B:

FIGS. 2A-B illustrate MAP Injection into a skin wound environment, in accordance with one or more embodiments of the invention. 20 µl of PEG-based MAP microbeads were injected and the tissue was retrieved 21 days after application. FIG. 2A shows the results from different fluorescent stains (DAPI, MAP-Alexa488, CD11b, and all three stains merged). FIG. 2B is a graph comparing CD11b response to MAP gel at day 21. The inflammatory reaction is significantly increased around the D-peptide containing particles. However, in particles that contain both L and D peptides (Hom) no activation is observed. This tissue was retrieved from a full thickness skin wound of a mouse model. The 1:1 50% D Het is a mixture of hydrogel particles where half of the particles are crosslinked with 100% L-chirality or D-chirality crosslinker. The 1:1 50% D Hom is a mixture of hydrogel particles where every particle is identically composed of 50% of the crosslinker being D-chirality and 50% being L-chirality. The hydrogels were prepared using a published technique (Griffin et al., "Accelerated Wound Healing by Injectable Microporous Gel Scaffolds Assembled from Annealed Building Blocks." *Nature Materials*. 2015).

Wounds were entirely closed by Day 10, meaning that any immune reaction was biased towards coming from the material and not an infection of the wound bed. The lack of a reaction to the 50% D-amino acid Hom indicates that the material must be more than 50% composed of D-chirality crosslinker to elicit a significant immune response.

CONCLUSION

This concludes the description of the illustrative embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

---

The invention claimed is:

1. A composition comprising:
   a polymeric hydrogel scaffold coupled to an adjuvant peptide comprising at least one D amino acid; and
   an immunogenic peptide comprising a viral, bacterial or cancer immunogen recognized by human immune cells, wherein:
   the adjuvant peptide and the immunogenic peptide are disposed in the polymeric hydrogel scaffold such that an in vivo immune reaction observed in human immune cells exposed to the immunogenic peptide is greater than an immune reaction observed in response to a control polymeric hydrogel scaffold composition that is identical to said polymeric hydrogel scaffold composition except that said control polymeric hydrogel scaffold composition comprises peptides formed only from L amino acids.

2. The composition of claim 1, wherein the polymeric hydrogel scaffold surrounds and encapsulates the immunogenic peptide.

3. The composition of claim 1, wherein the polymeric hydrogel scaffold forms pores in the composition, and the pores are between 1 μm and 50 μm such that immune cells can infiltrate the composition.

4. The composition of claim 1, wherein the hydrogel scaffold comprises at least one of:
   polyethylene glycol polymers;
   hyaluronic acid polymers;
   an RGD peptide;
   a Q peptide;
   a K peptide; or
   a Matrix Metallo-protease (MMP) peptide.

5. The composition of claim 1, wherein the adjuvant peptide comprises a crosslinker forming part of a backbone structure of the hydrogel scaffold.

6. The composition of claim 1, wherein the immunogenic peptide is disposed in the polymeric hydrogel scaffold such that a titer of IgG1 antibodies generated against the immunogenic peptide is at least 50% greater than a titer of IgG1 antibodies generated in response to the control polymeric hydrogel scaffold composition.

7. A method of modulating an immune response comprising contacting human immune cells with a composition of claim 1, so that the cells recognize the immunogenic peptide and initiate an immune response to the immunogenic peptide.

8. The method of claim 7, wherein the immune response comprises an infiltration of CD11b$^+$ cells to the site of the composition.

9. The method of claim 8, wherein an amount of CD11b$^+$ immune cells that infiltrate into the composition in vivo is at least 50% greater than an amount of CD11b$^+$ immune cells observed in response to the control polymeric hydrogel scaffold composition.

10. The method of claim 7, wherein the immune response comprises generating a titer of IgG1 antibodies that is at least 50% greater than a titer of IgG1 antibodies generated in response to the control polymeric hydrogel scaffold composition.

11. The method of claim 7, wherein the composition is disposed in a wound.

12. A method of increasing the tensile strength of new tissue forming in a wound comprising contacting the wound with a composition comprising a polymeric hydrogel scaffold and a peptide comprising at least one D amino acid, wherein said peptide comprises 16 amino acids.

13. The method of claim 12, wherein the tensile strength of tissue in the healed wound as measured by a tensiometer is at least 50% greater than a wound contacted with a control composition comprising the polymeric hydrogel scaffold coupled to a peptide having an identical amino acid sequence to the peptide of claim 12 but which comprises only L amino acids.

* * * * *